(12) United States Patent
Sikora et al.

(10) Patent No.: US 12,016,574 B2
(45) Date of Patent: *Jun. 25, 2024

(54) MICROFRACTURE APPARATUSES AND METHODS

(71) Applicant: ARTHROSURFACE, INC., Franklin, MA (US)

(72) Inventors: George J Sikora, Bridgewater, MA (US); Steven Ek, Bolton, MA (US)

(73) Assignee: ARTHROSURFACE, INC., Franklin, MA (US)

( * ) Notice: Subject to any disclaimer, the term of this patent is extended or adjusted under 35 U.S.C. 154(b) by 406 days.

This patent is subject to a terminal disclaimer.

(21) Appl. No.: 17/301,921

(22) Filed: Apr. 19, 2021

(65) Prior Publication Data

US 2022/0071643 A1 Mar. 10, 2022

Related U.S. Application Data

(63) Continuation of application No. 16/363,841, filed on Mar. 25, 2019, now Pat. No. 10,980,550, which is a continuation of application No. 14/916,242, filed as application No. PCT/US2014/054680 on Sep. 9, 2014, now Pat. No. 10,238,401.

(60) Provisional application No. 61/881,058, filed on Sep. 23, 2013.

(51) Int. Cl.
| A61B 17/16 | (2006.01) |
| A61B 17/34 | (2006.01) |
| A61B 50/33 | (2016.01) |
| A61B 17/00 | (2006.01) |
| A61B 50/30 | (2016.01) |

(52) U.S. Cl.
CPC ...... *A61B 17/1657* (2013.01); *A61B 17/1604* (2013.01); *A61B 17/3415* (2013.01); *A61B 17/3421* (2013.01); *A61B 17/3472* (2013.01); *A61B 50/33* (2016.02); *A61B 2017/00455* (2013.01); *A61B 2017/00942* (2013.01); *A61B 2050/3008* (2016.02); *A61B 2217/007* (2013.01)

(58) Field of Classification Search
CPC ............ A61B 17/1657; A61B 17/1604; A61B 17/3421

See application file for complete search history.

(56) References Cited

U.S. PATENT DOCUMENTS

| 2,423,511 A | 7/1947 | Luben et al. |
| 3,943,932 A | 3/1976 | Woo |
| 4,616,649 A | 10/1986 | Burns |
| 5,049,150 A | 9/1991 | Cozad |
| 5,356,420 A | 10/1994 | Czemecki et al. |

(Continued)

FOREIGN PATENT DOCUMENTS

| DE | 102011100695 | 11/2012 |
| EP | 0082081 | 12/1982 |

(Continued)

OTHER PUBLICATIONS

US 9,198,652 B2, 12/2015, Pilgeram (withdrawn)

(Continued)

*Primary Examiner* — Andrew Yang
(74) *Attorney, Agent, or Firm* — GOODWIN PROCTER LLP

(57) ABSTRACT

Embodiments of apparatuses and methods for microfracture (e.g., forming a plurality of microfractures in a bone to encourage cartilage regeneration).

20 Claims, 15 Drawing Sheets

(56) References Cited

U.S. PATENT DOCUMENTS

| | | | |
|---|---|---|---|
| 5,437,675 A | 8/1995 | Wilson |
| 5,667,509 A | 9/1997 | Westin |
| 5,741,288 A | 4/1998 | Rife |
| 5,741,291 A | 4/1998 | Yoo |
| 5,961,535 A | 10/1999 | Rosenberg et al. |
| 6,068,642 A | 5/2000 | Johnson et al. |
| 6,083,238 A | 7/2000 | Alexander et al. |
| 6,110,178 A | 8/2000 | Zech et al. |
| 6,146,385 A | 11/2000 | Torrie et al. |
| 6,193,721 B1 | 2/2001 | Michelson |
| 6,322,574 B1 | 11/2001 | Lloyd et al. |
| 6,322,575 B1 | 11/2001 | Schraga |
| 6,358,253 B1 | 3/2002 | Torrie et al. |
| 6,368,326 B1 | 4/2002 | Dankin et al. |
| 6,610,067 B2 | 8/2003 | Tallarida et al. |
| 6,692,502 B1 | 2/2004 | Ertl et al. |
| 6,712,822 B2 | 3/2004 | Re et al. |
| 6,960,214 B2 | 11/2005 | Burkinshaw |
| 7,029,479 B2 | 4/2006 | Tallarida et al. |
| 7,063,703 B2 | 6/2006 | Reo |
| 7,163,542 B2 | 1/2007 | Ryan |
| 7,241,302 B2 | 7/2007 | Sniffen et al. |
| 7,338,494 B2 | 3/2008 | Ryan |
| D581,534 S | 11/2008 | Dong et al. |
| 7,476,226 B2 | 1/2009 | Weikel et al. |
| 7,618,462 B2 | 11/2009 | Ek |
| 7,799,033 B2 | 9/2010 | Assell et al. |
| 7,942,881 B2 | 5/2011 | Torrie et al. |
| 7,967,605 B2 | 6/2011 | Goodis |
| 8,333,769 B2 | 12/2012 | Browne et al. |
| 8,394,102 B2 | 3/2013 | Garabedian et al. |
| 8,439,947 B2 | 5/2013 | Howard et al. |
| 8,821,494 B2 | 9/2014 | Pilgeram |
| 8,852,201 B2 | 10/2014 | Schmieding et al. |
| 8,911,474 B2 | 12/2014 | Howard et al. |
| 9,078,740 B2 | 7/2015 | Steiner et al. |
| 9,198,676 B2 | 12/2015 | Pilgeram et al. |
| 9,211,126 B2 | 12/2015 | Sikora et al. |
| 9,439,947 B2 | 9/2016 | Guha et al. |
| 9,510,840 B2 | 12/2016 | Sikora et al. |
| 9,572,587 B2 | 2/2017 | Sikora et al. |
| 9,918,721 B2 | 3/2018 | Sikora et al. |
| 10,039,554 B2 | 8/2018 | Sikora et al. |
| 2002/0032447 A1 | 3/2002 | Weikel et al. |
| 2003/0083665 A1 | 5/2003 | Re et al. |
| 2003/0135209 A1 | 7/2003 | Seedhom et al. |
| 2004/0073223 A1 | 4/2004 | Burkinshaw |
| 2004/0087956 A1 | 5/2004 | Weikel et al. |
| 2004/0133208 A1 | 7/2004 | Weikel et al. |
| 2004/0147932 A1 | 7/2004 | Burkinshaw et al. |
| 2004/0260300 A1 | 12/2004 | Gorensek et al. |
| 2005/0021067 A1 | 1/2005 | Kim |
| 2005/0038465 A1 | 2/2005 | Shraga |
| 2005/0043738 A1 | 2/2005 | Ryan |
| 2005/0137601 A1 | 6/2005 | Assell et al. |
| 2005/0165404 A1 | 7/2005 | Miller |
| 2005/0177071 A1 | 8/2005 | Nakayama et al. |
| 2005/0177168 A1 | 8/2005 | Brunnett et al. |
| 2005/0209620 A1 | 9/2005 | Du et al. |
| 2006/0111729 A1 | 5/2006 | Bacastow et al. |
| 2006/0116705 A1 | 6/2006 | Schraga |
| 2006/0235419 A1 | 10/2006 | Steinwachs et al. |
| 2006/0241627 A1 | 10/2006 | Reo |
| 2006/0241630 A1 | 10/2006 | Brunnett et al. |
| 2006/0264955 A1 | 11/2006 | Abdelgany |
| 2007/0270870 A1 | 11/2007 | Torrie et al. |
| 2008/0045964 A1 | 2/2008 | Mishra |
| 2008/0071282 A1 | 3/2008 | Assell et al. |
| 2008/0114365 A1 | 5/2008 | Sasing et al. |
| 2008/0132932 A1 | 6/2008 | Hoeppner et al. |
| 2008/0177266 A1 | 7/2008 | Metcalf et al. |
| 2008/0249481 A1 | 10/2008 | Crainich et al. |
| 2008/0262383 A1 | 10/2008 | Routhier et al. |
| 2008/0294167 A1 | 11/2008 | Schumacher et al. |
| 2008/0300510 A1 | 12/2008 | Schwyn et al. |
| 2009/0076520 A1 | 3/2009 | Choi |
| 2009/0076615 A1 | 3/2009 | Duggal et al. |
| 2009/0143782 A1 | 6/2009 | Levi |
| 2009/0143809 A1 | 6/2009 | Assell et al. |
| 2009/0274996 A1 | 11/2009 | Miller |
| 2009/0312782 A1 | 12/2009 | Park |
| 2010/0016816 A1 | 1/2010 | Schuessler et al. |
| 2010/0076440 A1 | 3/2010 | Pamichev et al. |
| 2010/0082033 A1 | 4/2010 | Germain |
| 2010/0087823 A1 | 4/2010 | Kondrashov |
| 2010/0094297 A1 | 4/2010 | Parmigiani |
| 2010/0168616 A1 | 7/2010 | Schraga et al. |
| 2010/0191195 A1 | 7/2010 | Kirshenbaum |
| 2010/0241124 A1 | 9/2010 | Housman et al. |
| 2010/0249786 A1 | 9/2010 | Schmieding et al. |
| 2010/0268282 A1 | 10/2010 | Trieu |
| 2010/0268285 A1 | 10/2010 | Tipirneni |
| 2010/0312246 A1 | 12/2010 | Browne et al. |
| 2010/0318139 A1 | 12/2010 | Beauchamp |
| 2011/0015675 A1 | 1/2011 | Howard et al. |
| 2011/0034930 A1 | 2/2011 | Buschmann et al. |
| 2011/0034945 A1 | 2/2011 | Paulos |
| 2011/0054612 A1 | 3/2011 | Dehnad et al. |
| 2011/0060349 A1 | 3/2011 | Cheng et al. |
| 2011/0063049 A1 | 3/2011 | Bradley et al. |
| 2011/0077653 A1 | 3/2011 | Haddock et al. |
| 2011/0238069 A1 | 9/2011 | Zajac et al. |
| 2011/0238126 A1 | 9/2011 | Soubeiran |
| 2011/0251615 A1 | 10/2011 | Truckai et al. |
| 2012/0071876 A1 | 3/2012 | Stoll et al. |
| 2012/0123485 A1 | 5/2012 | Dehnad et al. |
| 2012/0232558 A1 | 9/2012 | Berberich et al. |
| 2012/0271357 A1 | 10/2012 | Arthur et al. |
| 2013/0138046 A1 | 5/2013 | Feng |
| 2013/0317506 A1 | 11/2013 | Sikora et al. |
| 2014/0031825 A1 | 1/2014 | Torrie |
| 2014/0036656 A1 | 2/2014 | Chou et al. |
| 2014/0074102 A1 | 3/2014 | Mandeen et al. |
| 2014/0336656 A1 | 11/2014 | Rogers et al. |
| 2016/0022279 A1 | 1/2016 | Sikora et al. |
| 2016/0022280 A1 | 1/2016 | Sikora et al. |
| 2017/0303934 A1 | 10/2017 | Sikora et al. |
| 2018/0008285 A1 | 1/2018 | Sikora et al. |
| 2018/0271542 A1 | 9/2018 | Sikora et al. |
| 2019/0201007 A1 | 7/2019 | Sikora et al. |

FOREIGN PATENT DOCUMENTS

| | | |
|---|---|---|
| WO | WO 2003/057045 | 7/2003 |
| WO | WO 2009/129272 | 10/2009 |
| WO | WO 2011/014677 | 2/2011 |
| WO | WO 2012/103459 | 8/2012 |
| WO | WO 2013/134500 | 9/2013 |

OTHER PUBLICATIONS

Benthien, et al., "The treatment of chondral and osteochondral defects of the knee with autologous matrix-induced chondrogenesis (AMIC): method description and recent developments", Knee Surg Sports Traumatol Arthrosc, Aug. 2011, 19(8):1316-1319.

Extended European Search Report issued in corresponding European Application No. 15185091.4, dated Jan. 25, 2016.

Gill et al., "The Treatment of Articular Cartilage Defects Using the Microfracture Technique", *Journal of Orthopedic & Sports Physical Therapy*, 36(10), pp. 728-738, (2006).

Girolamo et al., "Treatment of chondral defects of the knee with one step matrix-assisted technique enhanced by autologous concentrated bone marrow: In vitro characterization of mesenchymal stem cells from iliac crest and subchondral bone", *Injury*, 41:1172-1177, 2010.

International Preliminary Report on Patentability Issued in Corresponding PCT Application No. PCT/2009/040581, dated Oct. 28, 2010.

International Search Report and Written Opinion issued in PCT Application No. PCT/US2013/029596, dated Jun. 19, 2013.

International Search Report and Written Opinion issued in PCT/US2014/054680, dated Jan. 22, 2015.

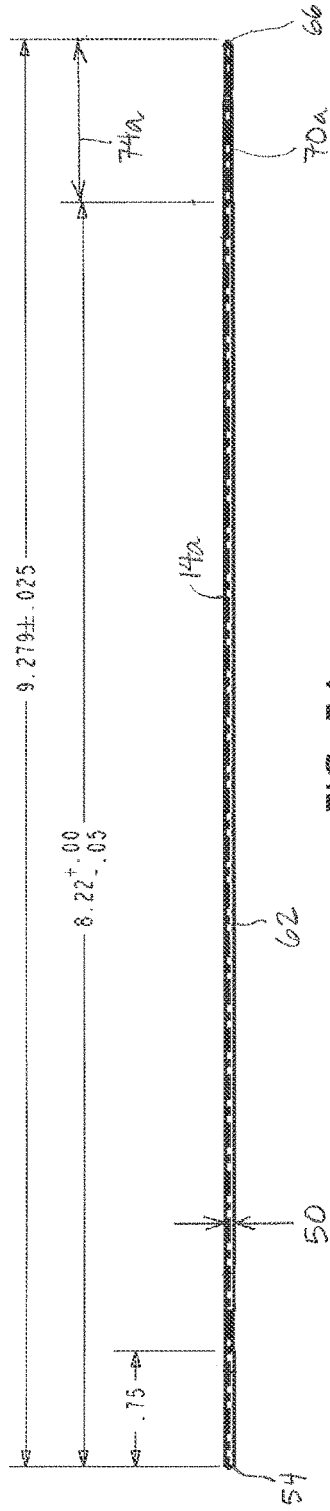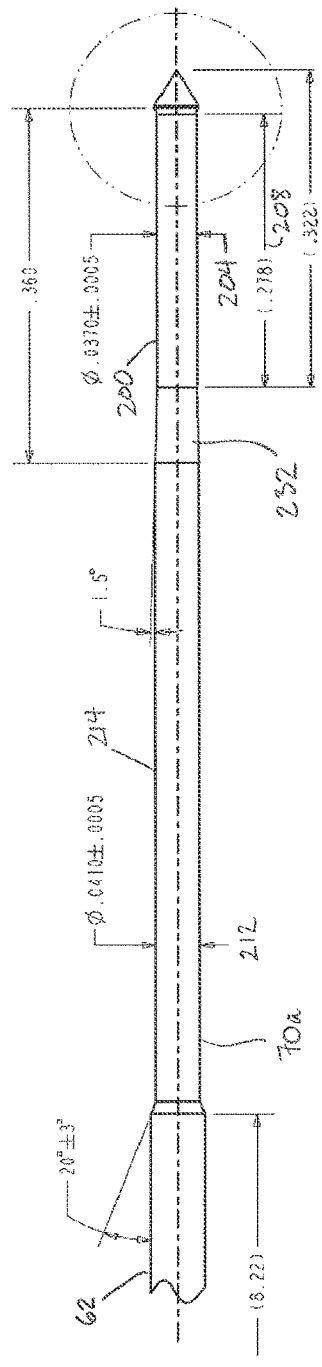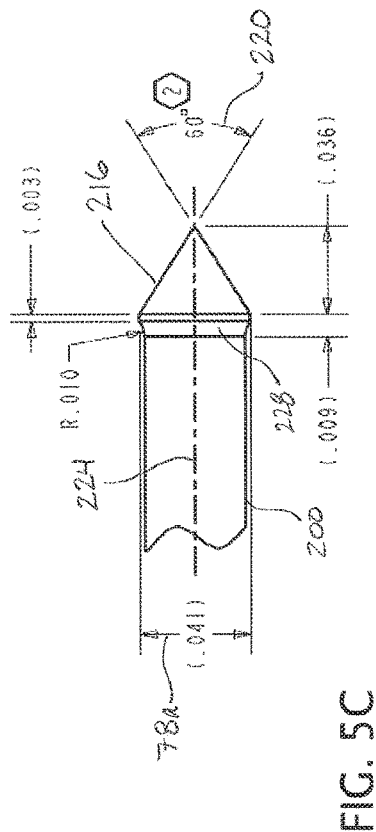
FIG. 5A
FIG. 5B
FIG. 5C

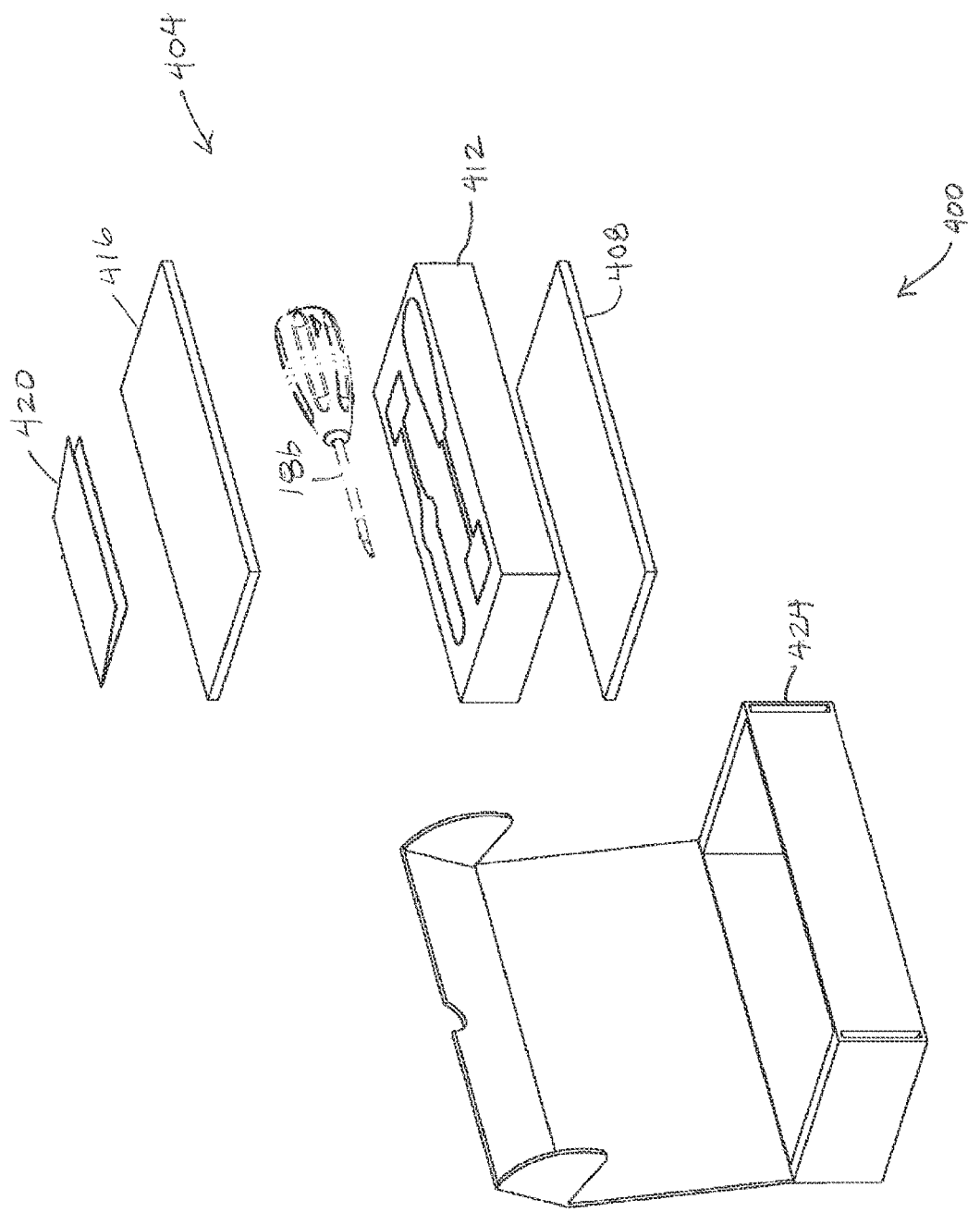

MICROFRACTURE APPARATUSES AND METHODS

CROSS-REFERENCE TO RELATED APPLICATIONS

This application is a continuation of U.S. patent application Ser. No. 16/363,841, filed Mar. 25, 2019, now issued U.S. Pat. No. 10,980,550, which is a continuation of U.S. patent application Ser. No. 14/916,242, filed Mar. 3, 2016, now issued U.S. Pat. No. 10,238,401, issued Mar. 26, 2019, which is a national phase application under 35 U.S.C. § 371 of International Patent Application No. PCT/US2014/054680, filed Sep. 9, 2014, which claims priority to U.S. Provisional Application No. 61/881,058, filed Sep. 23, 2013, the contents of each of which are incorporated by reference in their entirety.

BACKGROUND

1. Field of Invention

The present invention relates generally to orthopedic treatments, more particularly, but not by way of limitation, to devices and methods for creating microfractures (e.g., in subchondral bone).

2. Description of Related Art

Examples of treatment methods and apparatuses for creating microfractures in bone are disclosed in (1) J. P. Benthien, et al., *The treatment of chondral and osteochondral defects of the knee with autologous matrix-induced chondrogenesis (AMIC): method description and recent developments*, Knee Surg Sports Traumatol Arthrosc, August 2011, 19(8):1316-1319; (2) Thomas J. Gill, MD, et al., *The Treatment of Articular Cartilage Defects Using the Microfracture Technique*, Journal of Orthopaedic & Sports Physical Therapy, October 2006, 36(10):728-738; (3) L. de Girolamo, *Treatment of chondral defects of the knee with one step matrix-assisted technique enhanced by autologous concentrated bone marrow: In vitro characterisation of mesenchymal stem cells from iliac crest and subchondral bone*, Injury, Int. J. Care Injured 41 (2010) 1172-1177; (4) Pub. No. US 2009/0143782; (5) Pub. No. US 2005/0043738; (6) Pub. No. US 2005/0021067; and (7) Pub. No. US 2004/0147932.

SUMMARY

This disclosure includes embodiments of apparatuses, kits, and methods for creating microfractures in bone (e.g., subchondral bone). At least some of the present embodiments are configured to create a microfracture with a greater depth-to-width ratio than has been possible with known methods and apparatuses. For example, some embodiments are configured to create a microfracture in subchondral bone having a (e.g., first) transverse dimension (e.g., diameter) of less than 1.2 millimeters (mm) (e.g., between 1 mm and 1.1 mm, less than 1.1 mm, less than 1.05 mm, less than 1 mm), and a depth (or length) of at least 5 mm (e.g., 7 mm, 8 mm, 8-10 mm, or the like).

Some embodiments of the present apparatuses comprise: a cannula having a first end, a second end, and a channel extending between the first end and the second end, the channel having a first transverse dimension between the first end and the second end and having a second transverse dimension at the second end that is smaller than the first transverse dimension; and a penetrator having a distal end and a first transverse dimension, the penetrator configured to be disposed in the channel of the cannula such that the penetrator is movable between a retracted position and an extended position in which the distal end extends beyond the second end of the cannula by a penetration distance; where the penetrator is configured to be moved from the retracted position to the extended position substantially without rotation of the penetrator to form in subchondral bone a microfracture. In some embodiments, the first transverse dimension is substantially constant along a majority of the length of the channel. In some embodiments, the cannula has a primary portion and a distal portion between the primary portion and the second end, the distal portion configured such that: a second end of the channel is disposed at an angle relative to a first end of the channel; and the channel has a third transverse dimension at a proximal end of the distal portion that is larger than the second transverse dimension. In some embodiments, the third transverse dimension is substantially equal to the first transverse dimension.

Some embodiments of the present apparatuses comprise: a cannula having a first end, a second end, and a channel extending between the first end and the second end, the channel having a transverse dimension at the second end; a guide member having an opening and configured to be coupled to the second end of the cannula such that at least a portion of the opening is aligned with the channel, the opening having a transverse dimension that is smaller than the transverse dimension of the channel at the second end of the cannula; and a penetrator having a distal end and a first transverse dimension, the penetrator configured to be disposed in the channel of the cannula such that the penetrator is movable between a retracted position and an extended position in which the distal end extends beyond the guide member by a penetration distance; where the penetrator is configured to be moved from the retracted position to the extended position substantially without rotation of the penetrator to form in subchondral bone a microfracture. In some embodiments, the cannula has a primary portion and a distal portion between the primary portion and the second end, the distal portion configured such that: a second end of the channel is disposed at an angle relative to a first end of the channel, and the channel has a third transverse dimension at a proximal end of the distal portion that is larger than the second transverse dimension. In some embodiments, the third transverse dimension is substantially equal to the first transverse dimension.

Some embodiments of the present apparatuses comprise: a cannula having a first end, a second end, and a channel extending between the first end and the second end; a penetrator having a distal end and a first transverse dimension, the penetrator configured to be disposed in the channel of the cannula such that the penetrator is movable between a retracted position and an extended position in which the distal end extends beyond the second end of the cannula by a penetration distance, the penetrator having a guide portion spaced from the distal end, the guide portion having a second transverse dimension that is larger than the smallest transverse dimension of the penetrator; where the penetrator is configured to be moved from the retracted position to the extended position substantially without rotation of the penetrator to form in subchondral bone a microfracture. In some embodiments, the cannula has a primary portion and a distal portion between the primary portion and the second end, the distal portion configured such that a second end of the channel is disposed at an angle relative to a first end of the channel. In some embodiments, the distal portion of the cannula is configured such that the second end of the channel is aligned with the first end of the channel. In some embodiments, the guide portion includes two segments spaced apart from each other, each segment having a transverse dimension that is larger than the smallest transverse dimension of the penetrator.

Some embodiments of the present apparatuses comprise: a cannula having a first end, a second end, and a channel extending between the first end and the second end, the cannula having a primary portion and a distal portion between the primary portion and the second end, the distal portion configured such that a second end of the channel is aligned with and disposed at an angle relative to a first end of the channel; and a penetrator having a distal end and a first transverse dimension, the penetrator configured to be disposed in the channel of the cannula such that the penetrator is movable between a retracted position and an extended position in which the distal end extends beyond the second end of the cannula by a penetration distance; where the penetrator is configured to be moved from the retracted position to the extended position substantially without rotation of the penetrator to form in subchondral bone a microfracture. In some embodiments, the distal portion of the cannula includes a plurality of curved segments. In some embodiments, the distal portion of the cannula includes a first arcuate segment extending from a distal end of the primary portion, a second arcuate segment extending from and curving in a direction opposite to the curvature of the first arcuate segment, a third arcuate segment extending from and curving in the same direction as the curvature of the second arcuate segment, and a fourth linear segment extending from the third arcuate segment. In some embodiments, a first longitudinal axis of the fourth linear segment intersects a second longitudinal axis of the primary portion at the second end of the cannula. In some embodiments, the first longitudinal axis intersects the second longitudinal axis at an angle of between 30 and 60 degrees. In some embodiments, the primary portion of the cannula is substantially symmetrical around a longitudinal axis.

In some embodiments of the present apparatuses, the penetration distance is at least 5 times greater than the first transverse dimension of the channel. In some embodiments, the first transverse dimension is less than 1.2 millimeters (mm) (e.g., less than 1.1 mm). In some embodiments, the penetration distance is at least 5 millimeters (mm). In some embodiments, the penetrator is configured to be moved from the retracted position to the extended position substantially without rotation of the penetrator to form in subchondral bone a microfracture having a depth of at least 5 mm. In some embodiments, the penetrator is configured to be manually moved from the retracted position to the extended position. In some embodiments, the penetrator has an enlarged head, and the penetration distance is limited by the enlarged head contacting the cannula. In some embodiments, the penetrator comprises an elongated body and an enlarged head coupled to the elongated body. In some embodiments, the enlarged head is unitary with the elongated body. In some embodiments, the cannula includes a recessed portion and a shelf, the recessed portion extending from the first end of the cannula toward the second end of the cannula, the shelf disposed between the recessed portion and the second end of the cannula such that the penetration distance is limited by the enlarged head contacting the shelf. In some embodiments, the recessed portion has a depth that is at least as large as the penetration distance. In some embodiments, the enlarged head has a cylindrical shape with a length and a transverse dimension that is smaller than the length. In some embodiments, the enlarged head has a transverse dimension that is at least 90% of a corresponding transverse dimension of the recessed portion.

In some embodiments of the present apparatuses, the distal end of the penetrator is pointed. In some embodiments, the penetrator comprises at least one of a biocompatible metal, nickel-titanium alloy, stainless steel, and 316L stainless steel. In some embodiments, a coating is disposed on at least the penetration portion of the penetrator. In some embodiments, the coating is hydrophilic. In some embodiments, the coating comprises silver ions.

In some embodiments of the present apparatuses, the penetrator includes a primary portion and a penetration portion, the primary portion having a circular cross-section, the penetration portion disposed between the primary portion and the distal end, the penetration portion having a circular cross-section that is smaller than the circular cross-section of the primary portion. In some embodiments, the first transverse dimension is in the penetration portion, and a second transverse dimension smaller than the first dimension is between the first transverse dimension and the primary portion. In some embodiments, the penetration portion has a length and the second transverse dimension is substantially constant along part of the length of the penetration portion. In some embodiments, the penetration portion includes a narrow portion with at least one transverse dimension that is less than an adjacent transverse dimension of the penetration portion, such that the narrow portion is configured to reduce contact between the penetrator and a bone if the penetration portion is inserted into bone. In some embodiments, the penetrator includes a primary portion and a penetration portion disposed between the primary portion and the distal end, the first transverse dimension is in the penetration portion, and a second transverse dimension is between the first transverse dimension and the primary portion. In some embodiments, the second transverse dimension is smaller than the first transverse dimension. In some embodiments, the penetration portion has a length, and the second transverse dimension is substantially constant along part of the length of the penetration portion. In some embodiments, the first transverse dimension is closer to the distal end than to the primary portion. In some embodiments, the penetrator has a first cross-sectional area at the first transverse dimension, the penetrator has a second cross-sectional area at the second transverse dimension, and the first cross-sectional area is larger than the second cross-sectional area. In some embodiments, the penetrator has a first circular cross section at the first transverse dimension, and the penetrator has a second circular cross section at the second transverse dimension.

In some embodiments of the present apparatuses, the distal end includes a pointed tip with a cross-sectional shape defined by a tip angle of 60 degrees or greater. In some embodiments, the tip angle is bisected by a central longitudinal axis of the penetration portion. In some embodiments, the tip angle is greater than 90 degrees (e.g., greater than 120 degrees).

Some embodiments of the present apparatuses further comprise: a penetrator removal tab coupled to the penetrator and configured to retract the penetrator relative to the cannula. In some embodiments, the cannula includes a handle, the penetrator includes a flange, the penetrator removal tab includes an opening that is has at least one transverse dimension that is smaller than a transverse dimension of the flange; and the penetrator removal tab is configured to be disposed between the handle and the flange with the penetrator extending through the opening. In some embodiments, the penetrator removal tab includes a protrusion configured to extend toward the second end of the cannula and contact the handle to act as a fulcrum for pivoting the penetrator removal tab. In some embodiments, the cannula comprises a handle having an indicator indicative of the position of the distal portion of the cannula.

Some embodiments of the present apparatuses further comprise: an adapter having a first end configured to be coupled to the first end of the cannula, and a second end configured to be coupled to a syringe such that the syringe can be actuated to deliver solution to the channel of the cannula. In some embodiments, the first end of the adapter includes a tapered outer surface. In some embodiments, the second end of the adapter includes a luer lock. In some embodiments, the adapter has two or more protrusions configured for manipulation of the adapter.

Some embodiments of the present apparatuses comprise: a cannula having a first end, a second end, and a channel extending between the first end and the second end, the channel having a first transverse dimension between the first end and the second end and having a second transverse dimension at the second end that is smaller than the first transverse dimension; a penetrator having a distal end and a first transverse dimension, the penetrator configured to be disposed in the channel of the cannula such that the penetrator is movable between a retracted position and an extended position in which the distal end extends beyond the second end of the cannula by a penetration distance, the penetrator configured to be moved from the retracted position to the extended position to form in subchondral bone a microfracture; and an adapter having a first end configured to be coupled to the first end of the cannula, and a second end configured to be coupled to a syringe such that the syringe can be actuated to deliver solution to the channel of the cannula. In some embodiments, the first end of the adapter includes a tapered outer surface. In some embodiments, the second end of the adapter includes a luer lock.

Some embodiments of the present adapters comprise: a first end, a second end, and a channel extending between the first end and the second end, the first end having a tapered frustoconical outer surface configured to couple with a female receptacle, the second end having a luer lock, and first and second protrusions extending from an exterior surface of the adapter between the first end and the second end. In some embodiments, the first end has an inner diameter less than 5 mm. In some embodiments, the first end has at least one outer diameter less than 6 mm. In some embodiments, the first and second protrusions extend at least 3 mm from an exterior surface of the adapter. In some embodiments, the luer lock is configured to be connected to a syringe.

Some embodiments of the present kits comprise: an embodiment of the present apparatuses, where the penetrator is a first penetrator; and a second penetrator configured to be disposed in the channel of the cannula such that the second penetrator is movable between a retracted position and an extended position.

Some embodiments of the present kits comprise: a first one of the present penetrators (e.g., of one of the present apparatuses); and a package within which the first penetrator is sealed. Some embodiments further comprise: a second penetrator sealed in the package; where at least one of: the transverse dimension of the second penetrator is different than the transverse dimension of the first penetrator; and the second penetration distance is different than the first penetration distance. Some embodiments further comprise: an embodiment of the present cannulas (e.g., of one of the present apparatuses). Some embodiments further comprise; a tray within which the cannula is disposed.

Some embodiments of the present kits comprise: an embodiment of the present cannulas (e.g., of one of the present apparatuses); a re-usable, sterilizable tray; and a package within which the cannula and tray are sealed. Some embodiments further comprise: an embodiment of the present guide members (e.g., of one of the present apparatuses).

Some embodiments of the presents kits comprise: an embodiment of the present apparatuses; and a package within which the apparatus is disposed; where the apparatus is sterile.

Some embodiments of the present methods (e.g., of forming a microfracture in subchondral bone of a patient) comprise: disposing an embodiment of the present microfracture apparatuses adjacent to the subchondral bone; and advancing the penetrator relative to the cannula, substantially without rotation of the penetrator, until the distal end of the penetrator extends into the subchondral bone to form a microfracture having a depth greater than 5 mm. Some embodiments further comprise: repeating the steps of disposing and advancing to form a plurality of microfractures in the subchondral bone. In some embodiments, the apparatus further comprises a penetrator removal tab coupled to the penetrator and configured to retract the penetrator relative to the cannula, and the method further comprises: actuating the penetrator removal tab to retract the distal end of the penetrator from the bone. In some embodiments, the cannula includes a handle, the penetrator includes a flange, the penetrator removal tab includes an opening that is has at least one transverse dimension that is smaller than a transverse dimension of the flange; and the penetrator removal tab is configured to be disposed between the handle and the flange with the penetrator extending through the opening. In some embodiments, the penetrator removal tab includes a protrusion configured to extend toward the second end of the cannula and contact the handle to act as a fulcrum for pivoting the penetrator removal tab, and actuating the penetrator removal tab includes pivoting the penetrator removal tab around a point of contact between the protrusion and the handle. In some embodiments, the cannula comprises a handle having an indicator indicative of the position of the distal portion of the cannula. In some embodiments, the microfracture apparatus is disposed such that the second end of the cannula contacts the subchondral bone.

In some embodiments of the present methods, the penetrator is advanced manually. In some embodiments, the position of the second end of the cannula relative to the bone is substantially constant while advancing the penetrator. In some embodiments, the penetrator has an enlarged head, and the penetration distance is limited by the enlarged head contacting the cannula. In some embodiments, the cannula includes a recessed portion and a shelf, the recessed portion extending from the first end of the cannula toward the second end of the cannula, the shelf disposed between the recessed portion and the second end of the cannula such that the penetration distance is limited by the enlarged head contacting the shelf. In some embodiments, the recessed portion has a depth that is at least as large as the penetration distance. In some embodiments, the enlarged head has a cylindrical shape with a length and a transverse dimension that is smaller than the length. In some embodiments, the enlarged head has a transverse dimension that is at least 90% of a corresponding transverse dimension of the recessed portion. In some embodiments, the distal end of the penetrator is pointed. In some embodiments, the penetrator includes a primary portion and a penetration portion, the primary portion having a circular cross-section, the penetration portion disposed between the primary portion and the distal end, the penetration portion having a circular cross-section that is smaller than the circular cross-section of the primary portion. In some embodiments, the first transverse dimension is in the penetration portion, and a second transverse dimension smaller than the first dimension is between the first transverse dimension and the primary portion. In some embodiments, the penetration portion has a length and the second transverse dimension is substantially constant along part of the length of the penetration portion.

In some embodiments of the present methods, the penetrator includes a primary portion and a penetration portion disposed between the primary portion and the distal end, the first transverse dimension is in the penetration portion, and a second transverse dimension is between the first transverse dimension and the primary portion. In some embodiments, the second transverse dimension is smaller than the first transverse dimension. In some embodiments, the penetration portion has a length, and the second transverse dimension is substantially constant along part of the length of the penetration portion. In some embodiments, the first transverse dimension is closer to the distal end than to the primary portion. In some embodiments, the penetrator has a first cross-sectional area at the first transverse dimension, the penetrator has a second cross-sectional area at the second transverse dimension, and the first cross-sectional area is larger than the second cross-sectional area. In some embodiments, the penetrator has a circular cross section at the first transverse dimension, and has a circular cross section at the second transverse dimension. In some embodiments, the distal end includes a pointed tip with a cross-sectional shape defined by a tip angle of 60 degrees or greater. In some embodiments, the tip angle is bisected by a central longitudinal axis of the penetration portion. In some embodiments, the tip angle is greater than 90 degrees (e.g., greater than 120 degrees).

Some embodiments of the present methods (e.g., of treating a microfracture in subchondral bone of a patient) comprise: disposing an embodiment of the present (e.g., microfracture) apparatuses with the second end of the cannula adjacent an articular surface of a patient; moving the penetrator from the retracted position to the extended position to form a microfracture in the articular surface; removing the penetrator from the cannula; and injecting a solution to the microfracture through the channel of the cannula. In some embodiments, the solution is injected into the channel through an adapter (e.g., one of the present apparatuses). In some embodiments, the solution is injected into the channel from a syringe. In some embodiments, the solution is injected into the adapter from a syringe.

Some embodiments of the present methods (e.g., of treating a microfracture in subchondral bone of a patient) comprise: delivering a solution to a microfracture in an articular surface of a patient through a channel of a cannula of one of the present (e.g., microfracture) apparatuses having the second end of the cannula disposed adjacent the articular surface.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 5A depicts a side view of a second embodiment of the present penetrators.

FIGS. 5B and 5C depict enlarged side views of a penetration portion of the penetrator of the penetrator of FIG. 5A.

FIG. 9 depicts an exploded perspective view of a kit comprising an embodiment of the present apparatuses and a package for the apparatus.

DESCRIPTION OF ILLUSTRATIVE EMBODIMENTS

Figure 1A:
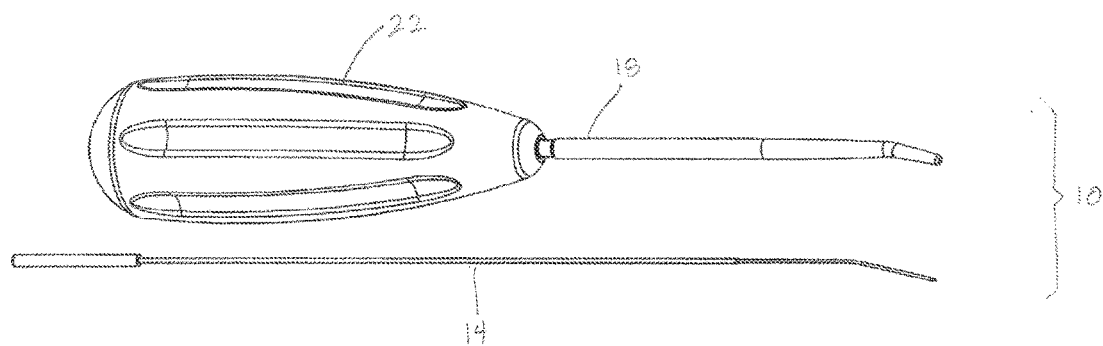
FIG. 1A depicts a perspective view of a first embodiment of the present apparatuses having a cannula and a penetrator, with the cannula shown next to the penetrator.
Figure 1B:
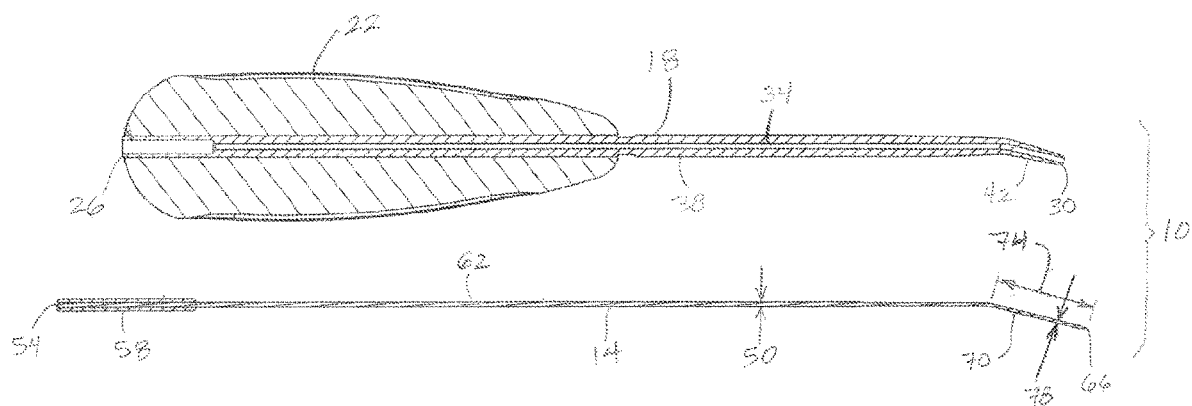
FIG. 1B depicts a cross-sectional view of the apparatus of FIG. 1A, with the cannula shown next to the penetrator.
Figure 1C:
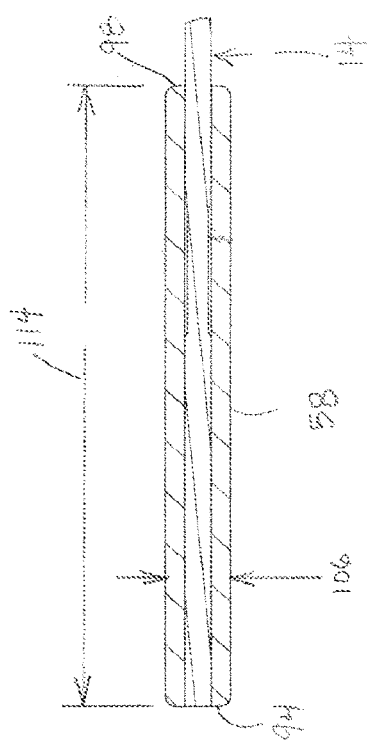
FIG. 1C depicts a cross-sectional view of an enlarged head of the penetrator shown in FIG. 1A.
Figure 1D:
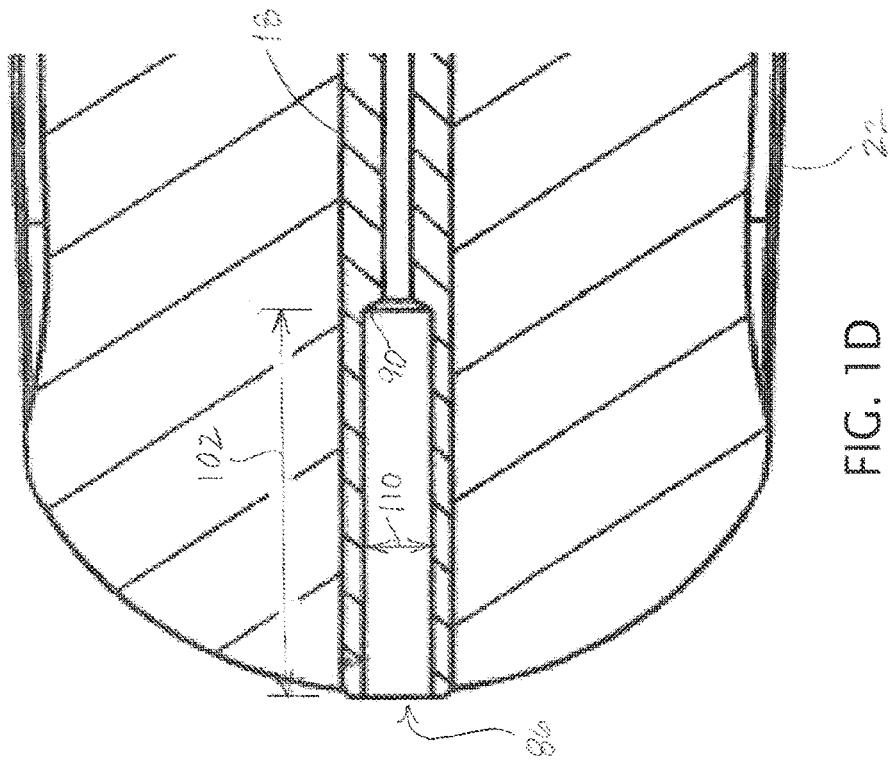
FIG. 1D depicts a cross-sectional view of a first end of the cannula shown in FIG. 1A.

Referring now to the drawings, and more particularly to FIGS. 1A-2C, shown therein and designed by the reference numeral 10 is one embodiment of the present apparatuses for creating microfractures in bone (e.g., subchondral bone). In the embodiment shown, apparatus 10 comprises a penetrator 14, a cannula 18, and a handle 22 coupled to cannula 18. In other embodiments (e.g., as shown in FIG. 3), handle 22 may be omitted. In the embodiment shown, cannula 18 has a first end 26, a second end 30, and a channel 34 extending between the first end and the second end. Such first and second ends should be understood as the locations of the beginning and end of the channel. In this embodiment, cannula 18 has a primary portion 38 and a distal portion 42, with primary portion 38 extending between first end 26 and distal portion 42 (e.g., a majority of the length of the cannula, as in the embodiment shown), and with distal portion 42 extending between primary portion 38 and second end 30. The distal portion can be configured such that a second end of the channel (at second end 30) is disposed at an angle relative to a first end of the channel (at first end 26). For example, in the embodiment shown, distal portion 42 is disposed at an angle 46 relative to the primary portion. In the embodiment shown, angle 46 is between 10 and 30 degrees (e.g., 20 degrees). In other embodiments, angle 46 can be any size that permits apparatus 10 to function as described in this disclosure (e.g., angle 46 can be equal to, or between any two of: 0, 10, 20, 30, 40, 45, 50, and/or 60 degrees). In other embodiments, angle 46 can be greater than 60 degrees (e.g., equal to, or between any two of: 60, 70, 80, 90, and/or more degrees). As a further example, distal portion 42 can include a curved or hooked shape such that angle 46 is effectively larger than 90 degrees (e.g., equal to, or between any two of: 90, 120, 150, 180, and/or 180 degrees).

Primary portion 38 has a transverse dimension 50 (e.g., a diameter, in the embodiment shown). Penetrator 14 and cannula 18 can comprise any suitable material that permits the apparatus to function as described in this disclosure (e.g., and permits the penetrator and the cannula to be sterilized). For example, in some embodiments, penetrator 14 comprises nickel-titanium alloy (e.g., Nitinol), and/or cannula 18 comprises metal, such as stainless steel (e.g., a surgical stainless steel). Embodiments of the present cannulas are rigid and configured not to flex or bend during use. In other embodiments, penetrator 14 can comprise a biocompatible metal such as stainless steel (e.g., 316L stainless steel).

In the embodiment shown, penetrator 14 has a proximal end 54, an enlarged head 58 adjacent proximal end 54, a primary portion 62, a distal end 66 (e.g., pointed distal end 66, as shown), and a penetration portion 70 adjacent distal end 66. In this embodiment, penetration portion 70 has a length 74 that is a minority of the length of penetrator 14 between proximal end 54 and distal end 66. In some embodiments, penetrator 14 has a transverse dimension of less than 1.2 mm (e.g., between 1 mm and 1.1 mm; less than 1.1 mm, less than 1.05 mm, less than 1 mm; less than, or between any two of, 0.5, 0.6, 0.7, 0.8, 0.9, and/or 1 mm). For example, in the embodiment shown, penetration portion 70 has a circular cross-section with a diameter 78 of between 0.7 and 0.8 mm (e.g., 0.78 mm). In some embodiments, penetration portion 70 has a circular cross-section with a diameter of between 1 and 1.1 mm (e.g., 1.04 mm). Penetrator 14 is configured to be disposed in channel 34 of cannula 18 such that penetrator 14 is movable between a (1) retracted position (e.g., in which distal end 66 of the penetrator does not extend beyond second end 30 of the cannula) and (2) an extended position in which distal end 66 of the penetrator extends beyond second end 30 of the cannula by a penetration distance 82. In some embodiments, penetration distance 82 is at least (e.g., greater than) 5 mm (e.g., 7 mm, 8 mm, 8-10 mm, more than 10 mm) and/or at least (e.g., greater than) 5 times (e.g., greater than, or between any two of: 6, 7, 8, 9, 10, or more times) a transverse dimension (e.g., diameter) of penetrator 14 (e.g., diameter 78 of penetration portion 70). For example, in the embodiment shown, penetration distance 82 is between 8 mm and 10 mm (e.g., 10 mm), which is greater than 12 times diameter 78. In the embodiment shown, diameter 50 of primary portion 38 is larger than diameter 78 of penetration portion 70. In some embodiments, diameter 50 is also less than 1.2 mm (e.g., between 1 mm and 1.1 mm, less than 1.1 mm, less than 1.05 mm). In some embodiments, diameter 50 is substantially equal to diameter 78. In some embodiments, penetrator 14 comprises a central wire defining diameter 78 that is encircled or encased by an outer tubing (e.g., metallic tubing, plastic shrink wrap, and/or the like along the length of primary portion 62 to define transverse dimension 50.

In some embodiments, a coating is disposed on at least penetration portion 70 of penetrator 14 (the coating may also be disposed on primary portion 62 of the penetrator). In some embodiments, the coating is hydrophilic. Examples of hydrophilic coatings include Hydro-Silk coatings available from TUA Systems of Florida (U.S.A.). In some embodiments, the coating comprises silver ions. In some embodiments, the coating comprises one or more active ingredients configured to elicit or stimulate a biological response in (e.g., bone or cartilage) tissue, such as, for example, growth factor(s), anticoagulant(s), protein(s), and/or the like. Such coatings can be applied as known in the art for the materials used in particular embodiments.

In the embodiment shown, cannula 18 is configured to provide lateral support for penetrator 14, such as to prevent the penetrator from bending or buckling while being driven into the hard subchondral bone. For example, in the embodiment shown, diameter 50 of primary portion 62 of the penetrator is nearly as large as (e.g., greater than, or between any two of: 95, 96, 97, 98, 99, and or 100 percent of) the diameter of channel 34, and diameter 78 of penetration portion 70 is greater than 75% (e.g., greater than, or between any two of: 75, 80, 85, 90, 95, and/or 100 percent of) the diameter of channel 34 (e.g., the diameter of channel 34 adjacent second end 30 of the cannula). In some embodiments, penetrator 14 is substantially straight prior to being disposed in channel 34 of cannula 18, such that inserting the penetrator into the cannula causes the penetration portion 70 of the penetrator to be angled relative to primary portion 62. In some such embodiments, penetrator 14 may be resilient enough to (e.g., at least partially) return to its straight shape after removal from the cannula.

In some embodiments, penetrator 14 is configured to be moved or advanced (e.g., substantially without rotation of the penetrator) from the retracted position to the extended position (FIG. 2B) to form a microfracture in subchondral bone (e.g., in a patient's knee or shoulder joint), the microfracture having a depth of at least (e.g., more than) 5 mm (e.g., 7 mm, 8 mm, 8-10 mm, more than 10 mm) and/or at least (e.g., greater than) 5 times (e.g., greater than, or between any two of: 6, 7, 8, 9, 10, or more times) a transverse dimension (e.g., diameter) of penetrator 14 (e.g., diameter 78 of penetration portion 70). For example, in the embodiment shown, penetrator 14 is configured to be moved or advanced (e.g., substantially without rotation of the penetrator, which includes no rotation up to rotation of less than one full revolution clockwise and/or counterclockwise from the position at which distal end 66 of the penetrator first contacts the bone) from the retracted position to the extended position (FIG. 2B) to form a microfracture in subchondral bone (e.g., in a patient's knee or shoulder joint), the microfracture having a depth of between 8 mm and 10 mm (e.g., 10 mm), which is greater than 12 times diameter 78. In the embodiment shown, penetrator 14 is configured to be moved or advanced manually to the extended position. As used in this disclosure, moved or advanced "manually" means without the assistance of an external energy source other than that provided by a user. For example, if the penetrator is moved or advanced with a battery-powered or spring-driven driver, it would not be "manually." Conversely, the penetrator would be moved or advanced "manually" if a mallet, hammer, or other tool is swung by a user (e.g., in the user's hand) to impact first end 26 of the penetrator. In some embodiments, the present apparatuses are configured such that the penetrator can (but need not) be rotated as it is advanced or moved from the retracted position to the advanced position. For example, a portion of the penetrator (e.g., enlarged head 58) can be disposed in the chuck of a drill such that the drill can rotate the penetrator. In such embodiments, the penetrator may (but need not) be substantially straight or axial (without bends) along its entire length (e.g., prior to being disposed in a cannula with an angled distal portion).

Figure 2A:
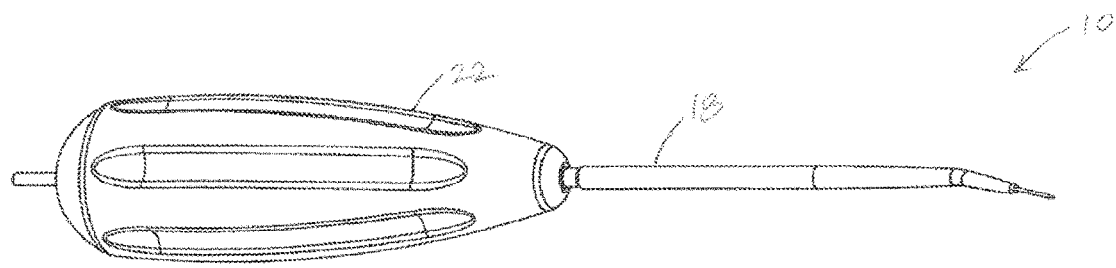
FIG. 2A depicts a perspective view of the apparatus of FIG. 1A, with the penetrator shown in the cannula.
Figure 2B:
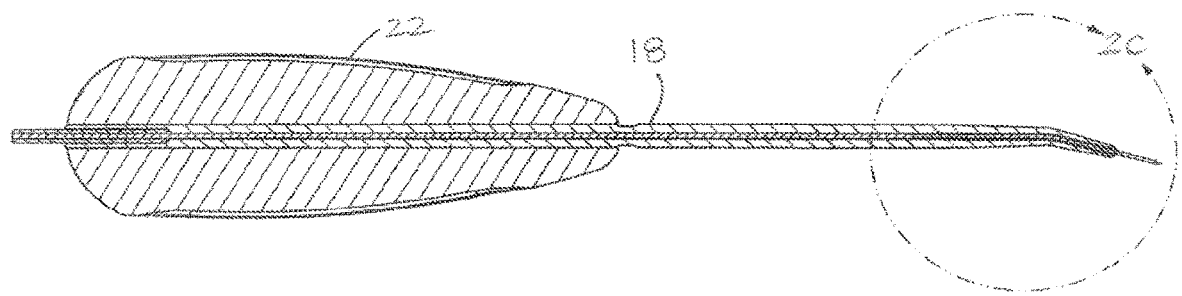
FIG. 2B depicts a cross-sectional view of the apparatus of FIG. 1A, with the penetrator shown in the cannula.
Figure 2C:
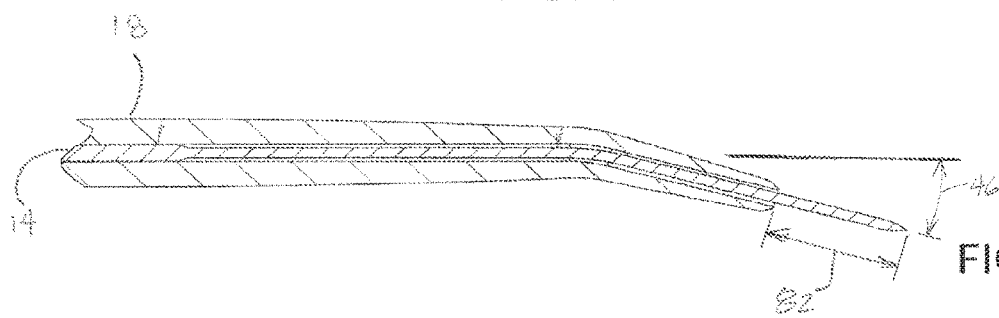
FIG. 2C depicts a cross-sectional view of a portion of the apparatus of FIG. 1A that includes a second end of the cannula and a distal end of the penetrator, with the penetrator shown in the cannula.
Figure 3:
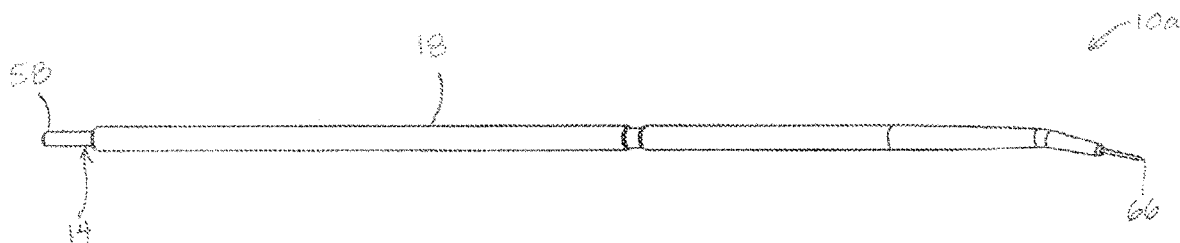
FIG. 3 depicts a perspective view of a second embodiment of the present apparatuses.

In the embodiment shown, penetration distance 82 (and the depth of the microfracture the apparatus is configured to create) is limited by enlarged head 58 contacting the cannula (e.g., penetration distance is maximized when enlarged head 58 contacts the cannula, as shown in FIG. 2B). For example, in the embodiment shown, cannula 18 includes a recessed portion 86 and a shelf 90. As shown, recessed portion 86 extends from first end 26 toward second end 30 (inwardly), and shelf 90 is disposed between recessed portion 86 and second end 30 such that penetration distance 82 is limited by enlarged head 58 contacting shelf 90. For example, in the embodiment shown, enlarged head 58 has a cylindrical (e.g., circular cylindrical, as shown) with a first end 94 and a second end 98, and is configured such that second end 98 contacts shelf 90 when the penetrator is in the extended position relative to the cannula (FIG. 2B). In some embodiments, recessed portion 86 can be configured to maintain the orientation or alignment of enlarged head 58 as the penetrator is moved or advanced from the retracted position to the extended position. For example, in some embodiments, recessed portion 58 has a depth 102 that is at least as large as (e.g., is greater than, or between any two of: 100, 110, 120, 130, 140, 150, or more percent of) penetration distance 82 (e.g., such that enlarged head 58 is at least partially within recessed portion 86 when distal end 66 extends beyond second end 30 of the cannula), and/or enlarged head 58 has a transverse dimension (e.g., diameter) that is at least 90% (e.g., greater than, or between any two of: 90, 92, 94, 96, 98, and/or 100 percent) of a corresponding transverse dimension of recessed portion 86 (e.g., such that cannula 18 limits tilting of enlarged head 58 relative to cannula 14, and/or limits misalignment of enlarged head 58 relative to primary portion 62 of the penetrator).

For example, in the embodiment shown, depth 102 of recessed portion 58 is between 175% and 250% (e.g., between 200% and 225%) of penetration distance 82. In this embodiment, enlarged head 58 and recessed portion 86 each has a circular cross section, and enlarged head 58 has a diameter 106 that is between 90% and 100% (e.g., between 95% and 100%) of diameter 110 of recessed portion 86. In some embodiments, a length 114 of enlarged head 58 is at least 150% (e.g., at least, or between any two of: 150, 175, 200, 225, 250, 300, or more percent) of penetration distance 82. For example, in the embodiment shown, length 114 is over 300% of penetration distance 82, such that a portion of enlarged head 58 that is at least as long as penetration distance 82 is disposed in recessed portion 86 when distal end 66 of the penetrator is even with second end 30 of the cannula (and the orientation of enlarged head 58 relative to cannula 18 is thereby maintained). In some embodiments, enlarged head 58 has an elongated shape such that length 114 is greater than (e.g., greater than, or between any two of: 2, 3, 4, 6, 8, or more times) diameter 106. For example, in the embodiment shown, length 114 is between 8 and 12 times diameter 106.

FIG. 3 depicts a second embodiment 10a of the present apparatuses. Apparatus 10a is substantially similar to apparatus 10, with the exception that apparatus 10a does not include a handle (e.g., handle 22).

Embodiments of the present kits can comprise one or more of the present cannulas (e.g., cannula 14) and a reusable tray or other container in a package (e.g., a sealed pouch or the like), where both the cannula(s) and the tray are or can be sterilized (and can be re-sterilized in advance of being re-used). Both the tray and the package may be rectangular in shape. In addition, some embodiments of the present kits can also include two or more penetrators configured to create different microfractures. For example, some embodiments of the present kits comprise one or more of the present cannulas, a sterlizable tray, a first penetrator configured to have a penetration distance of between 5 mm and 8 mm when used in combination with the cannula, and a second penetrator configured to have a penetration distance greater than 8 mm when used in combination with the cannula. More specifically, some embodiments of the present kits may include a package (e.g., a box or a flexible package) that comprises sterilized versions of these items. Other embodiments of the present kits comprise one or more of the present penetrators (e.g., a single penetrator or two penetrators having different penetration depths, different tip diameters, different tip shapes, and/or the like) that are sterile and disposed in a package. Embodiments of the present kits may also include, in more specific embodiments, instructions for use, which instructions may be inside the package (e.g., as an insert) or outside the package (such as a sticker on the package).

Figure 4A:
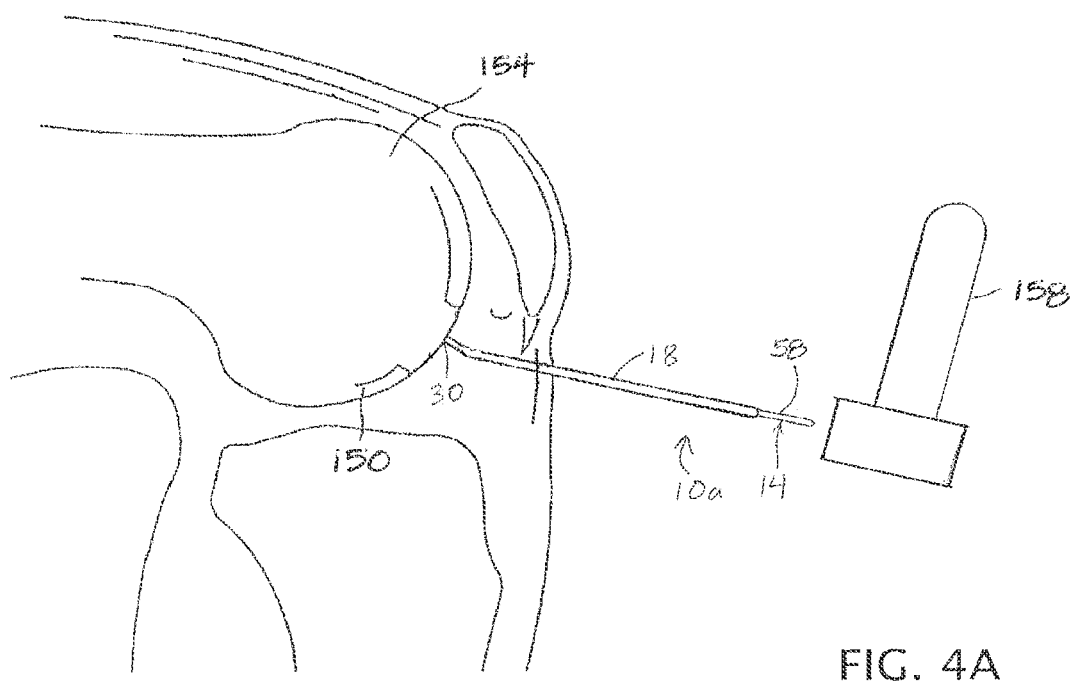
FIGS. 4A and 4B depict perspective view of the apparatus of FIG. 3 positioned for use relative to a patient's knee, and are not drawn to scale.
Figure 4B:
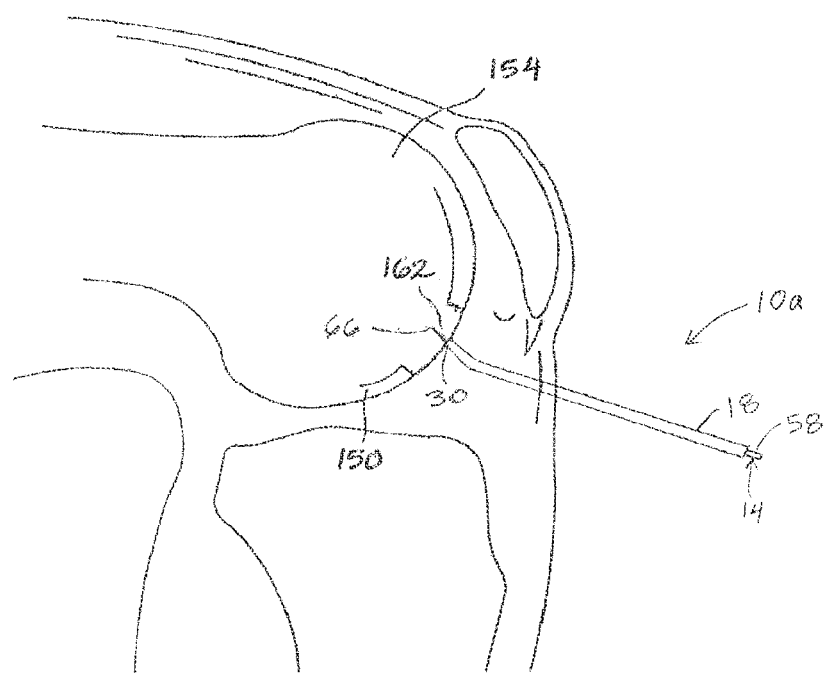

FIGS. 4A and 4B depict an example of the present methods (e.g., using embodiment 10a of the present apparatuses). Some embodiments of the present methods comprise: disposing an embodiment of the present microfracture apparatuses (e.g., 10, 10a) adjacent to subchondral bone of a patient (e.g., in the knee, shoulder, or other joint). For example, in the embodiment shown, apparatus 10a is disposed adjacent to subchondral bone of articular surface 150 in a patient's knee 154 (e.g., with second end 30 of cannula 18 in contact with the subchondral bone, as shown). Some embodiments further comprise moving or advancing penetrator 14 relative to cannula 18 (e.g., from FIG. 4A to FIG. 4B) until distal end 66 of the penetrator extends into the subchondral bone (as in FIG. 4B) to form a microfracture having a depth of at least 5 mm. For example, in the embodiment shown, penetrator 18 is manually advanced substantially without rotation of the penetrator by striking or impacting proximal end 54 of the penetrator with a mallet 158 until distal end 66 extends into the subchondral bone by a distance of, and forms a microfracture 162 having a depth of, 10 mm. In the embodiment shown, the position of second end 30 of the cannula relative to the subchondral bone remains substantially constant while advancing the penetrator into the bone. In some embodiments of the present methods, the apparatus is repeatedly disposed adjacent the bone (e.g., with second end 30 of the cannula in contact with the subchondral bone and/or in contact with cartilage, such as, for example, cartilage around the perimeter of a lesion), and the penetrator is repeatedly advanced into the subchondral bone to form a plurality of microfractures (e.g., having substantially the same depths). In some embodiments, the present methods can be performed on and/or in the surfaces of other joints, such as, for example, the shoulder, the ankle, the hip, and/or the patellofemoral joint within the knee.

Referring now to FIGS. 5A-5C, a second embodiment 14a of the present penetrators is shown. Penetrator 14a is similar in many respects to penetrator 14. For example, penetrator 14a has a proximal end 54, a primary portion 62, a distal end 66 (e.g., pointed distal end 66, as shown), and a penetration portion 70a adjacent distal end 66. While not shown in FIG. 5A, penetrator 14a can also include an enlarged head (similar to enlarged head 58 of penetrator 14). In this embodiment, penetration portion 70a has a length 74a that is a minority of the length of penetrator 14a between proximal end 54 and distal end 66. Similarly, in some embodiments, penetrator 14a has a transverse dimension of less than 1.2 mm (e.g., between 1 mm and 1.1 mm; less than 1.1 mm, less than 1.05 mm, less than 1 mm; less than, or between any two of, 0.5, 0.6, 0.7, 0.8, 0.9, and/or 1 mm). For example, in the embodiment shown, penetration portion 70a has a circular cross-section with a diameter 78a of between 1 and 1.2 mm (e.g., 1.04 mm). As with penetrator 14, penetrator 14a is configured to be disposed in channel 34 of cannula 18 such that penetrator 14 is movable between a (1) retracted position (e.g., in which distal end 66 of the penetrator does not extend beyond second end 30 of the cannula) and (2) an extended position in which distal end 66 of the penetrator extends beyond second end 30 of the cannula by a penetration distance 82, which may, for example, be at least (e.g., greater than) 5 mm (e.g., 7 mm, 8 mm, 8-10 mm, more than 10 mm) and/or at least (e.g., greater than) 5 times (e.g., greater than, or between any two of: 6, 7, 8, 9, 10, or more times) a transverse dimension (e.g., diameter) of penetrator 14 (e.g., diameter 78a of penetration portion 70).

For example, in the embodiment shown, penetration distance 82 is between 8 mm and 10 mm (e.g., 10 mm), which is greater than 7 times diameter 78a. In some embodiments, the length of the penetration portion is greater than a penetration distance 82 for which the penetrator is designed. For example, in the embodiment shown, length 74a is greater than the penetration distance 82 (e.g., and greater than the sum of penetration distance 82 and the length of distal portion 42 of cannula 14 and/or cannula 14a). In the embodiment shown, diameter 50 of primary portion 38 is larger than diameter 78a of penetration portion 70a, and/or equal to or greater than 1.2 mm (e.g., substantially equal to 1.27 mm) and/or less than 2.0 mm. In some embodiments, diameter 50 is also less than 1.2 mm (e.g., between 1 mm and 1.1 mm, less than 1.1 mm, less than 1.05 mm). In some embodiments, diameter 50 is substantially equal to diameter 78.

In some embodiments, penetrator 14 comprises a central wire defining transverse dimension 78a that is encircled or encased by an outer tubing (e.g., metallic tubing, plastic shrink wrap, and/or the like along the length of primary portion 62a to define transverse dimension 50a.

As shown in FIGS. 5B and 5C, however, penetration portion 70a differs from penetration portion 70 in that penetration portion 70a is configured to reduce (e.g., relative to that of penetration portion 70) the force required to insert distal end 66 into a bone, and to reduce (e.g., relative to that of penetration portion 70) the force required to remove distal end 66 from the bone. For example, in the embodiment shown, penetration portion 70 includes a narrow portion 200 between distal end 66 and primary portion 62, with narrow portion 200 being narrower in at least one transverse dimension than primary portion 62. In this embodiment, narrow portion 200 is configured to reduce the surface area of penetration portion 70a that is in contact with bone when the penetration portion is driven into a bone. For example, the enlarged part of penetration portion 70a adjacent distal end 66 (and corresponding to first transverse dimension 78a) creates a path through the bone during insertion that is larger than narrow portion 200, such that at least a part of narrow portion 200 is not (at least initially) in contact with the bone. Even if penetration portion 70a remains in the bone for a sufficient time for the bone to rebound towards narrow portion 200, the reduced transverse dimension of narrow portion 200 may reduce the interface pressure between the penetrator and the rebounded bone material. This reduced contact and/or reduced interface pressure can reduce the force required to remove distal end 66 from the bone (e.g., relative to the force required to remove from the same type of bone penetration portion 70 of penetrator 14, which has a circular cylindrical shape with constant diameter and cross-section along the length of penetration portion 70—i.e., does not include narrow portion 200).

For example, in the embodiment shown, transverse dimension 78a is a first transverse dimension in the penetration portion, and a second transverse dimension 204 that is smaller than first transverse dimension 78a is between primary portion 62 and first transverse dimension 78a (in penetration portion 70a, as shown). In some embodiments, second transverse dimension 204 is substantially constant along part of length 74. For example, in the embodiment shown, narrow portion 200 has a length 208 along which second transverse dimension 204 is substantially constant. In the embodiment shown, length 208 is between 20 percent and 35 percent of length 74a of penetration portion 70a. In other embodiments, length 208 can be any suitable fraction or percentage of length 74a (e.g., less than any one of, or between any two of, 5, 10, 15, 20, 25, 30, 35, 40, 45, and/or 50 percent). In some embodiments, first transverse dimension 78a is adjacent distal end 66 (i.e., closer to distal end 66 than to primary portion 62). For example, in the embodiment shown, the distance between distal end 66 and narrow portion 200 is less than length 208 of the narrow portion. In other embodiments, narrow portion can be disposed at any suitable position along the length of penetration portion 70a. In the embodiment shown, penetration portion 70a further includes a third transverse dimension 212 between narrow portion 200 and primary portion 62. In this embodiment, third transverse dimension 212 is substantially equal to first transverse dimension 78a, but may differ in other embodiments. In the embodiment shown, third transverse dimension is substantially constant along a proximal segment 214 of penetration portion 70a.

In some embodiments, penetrator 14a has a first cross-sectional shape and/or area at first transverse dimension 78a, a second cross-sectional shape and/or area at second transverse dimension 204, and the first cross-sectional shape and/or area is larger than (e.g., and, as shown, concentric to) the second cross-sectional shape and/or area. For example, in the embodiment shown, penetrator 14a has a first circular cross section at first transverse dimension 78a, and a second circular cross section at second transverse dimension 204 (e.g., with the first circular cross-section being substantially concentric with the second circular cross-section, as shown). In this embodiment, penetrator 14a also has a circular cross-section at third transverse dimension 212. In other embodiments, the penetrator, the penetration portion, and/or the narrow portion can have any suitable cross-sectional shapes (e.g., circle, square, triangular, rectangular, star, and/or the like), whether similar or dissimilar (e.g., the cross-sectional shape of the narrow portion may differ from the cross-sectional shape of the remainder of the penetration portion), such that the cross-sectional shape of the surface of area of the narrow portion that contacts bone during insertion is reduced. For example, in some embodiments, the penetration portion can have a circular cross-section and the narrow portion can have a rectangular cross-section. In other embodiments, narrow portion 200 may be fluted.

In the embodiment shown, penetration portion 70a also differs from penetration portion 70 in that distal end 66 is configured to reduce (e.g., relative to that of penetration portion 70) the force required to insert distal end 66 into a bone, and to reduce (e.g., relative to that of penetration portion 70) the force required to remove distal end 66 from the bone. For example, in the embodiment shown, distal end 66 includes a pointed tip 216 with a cross-sectional shape defined by a tip angle 220 of 60 degrees or greater (e.g., substantially equal to 60 degrees, as shown). For example, in the embodiment shown, pointed tip 216 has a conical shape having a cross-sectional shape that is bisected by a central longitudinal axis 224 of penetration portion 70a. In other embodiments, pointed tip 216 can have any suitable shape (e.g., a triangular or rectangular pyramid). In some embodiments, tip angle 220 is greater than 60 degrees, greater than 90 degrees, and/or greater than 120 degrees (e.g., equal to 180 degrees, or substantially perpendicular to a longitudinal axis of an adjacent portion of penetration portion 70a). For example, a tip angle 220 of 60 degrees, as shown, reduces the length of the cone that defines pointed tip relative to the 30 degree tip angle of penetrator 14, and thereby reduces the surface area of the cone that is available to contact bone during insertion and removal. Likewise, further increases in tip angle 220 will further reduce the surface area of a conical pointed that is available to contact bone. In the embodiment shown, penetration portion 70a further includes a first radiused portion 228 (which may instead be linearly tapered) between pointed tip 216 (and first transverse dimension 78a) and narrow portion 200, and a second tapered portion 232 (which may instead be radiused) between proximal segment 214 and narrow portion 200, to reduce likelihood of the transitions in transverse dimension resulting in points along penetration portion 70a that might otherwise catch or resist insertion or removal of distal end 66 into or from bone. In other embodiments, the tip can be rounded and/or can be defined by a single (e.g., planar) facet extending across the entire cross-section of the penetration portion.

In the embodiment shown, penetrator 14a is substantially straight prior to being disposed in channel 34 of cannula 18 or cannula 18b, such that inserting the penetrator into the cannula causes the penetration portion 70a of the penetrator to bend within channel 34 (between primary portion 38 or 38a and distal portion 42 or 42a). In some such embodiments, penetrator 14a may be resilient enough to (e.g., at least partially) return to its straight shape after removal from the cannula.

Figure 6:
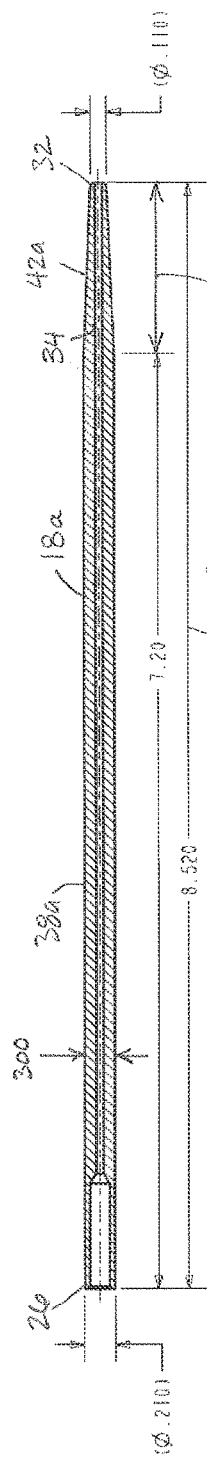
FIG. 6 depicts a side cross-sectional view of a second embodiment of the present cannulas.

FIG. 6 depicts a side cross-sectional view of a second embodiment 18a of the present cannulas. Cannula 18a is similar in many respects to cannula 18. For example, cannula 18a has a first end 26, a second end 30, and a channel 34 extending between the first end and the second end. Such first and second ends should be understood as the locations of the beginning and end of the channel. In this embodiment, cannula 18 has a primary portion 38a and a distal portion 42a, with primary portion 38a extending between first end 26 and distal portion 42a (e.g., a majority of the length of the cannula, as in the embodiment shown), and with distal portion 42a extending between primary portion 38 and second end 30. In the embodiment shown, cannula 18a differs from cannula 18 in that in cannula 18a, distal portion 42a is not angled relative to primary portion 38a (distal portion 42a and primary portion 38a share a common central longitudinal axis). Primary portion 38a has a transverse dimension 300 (e.g., a diameter, in the embodiment shown). In the embodiment shown, distal portion 42a is tapered between primary portion 38a and second end 30, as shown. In this embodiment distal portion 42a has a length 304 that is less than a length 308 of cannula 18a (e.g., less than 20 percent of length 308). In other embodiments, the relative lengths of primary portion 38a and distal portion 42a can be any suitable sizes for various procedures and/or for patients of various ages and/or sizes. In some embodiments of the present methods, cannula 18a is bent to form a cannula with an angled distal portion, as described below.

Figure 7A:
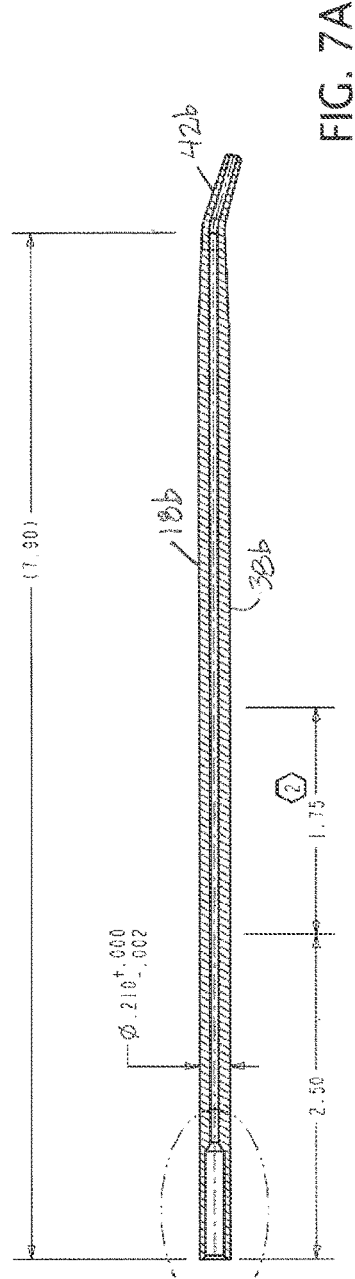
FIG. 7A depicts a side cross-sectional view of a third embodiment of the present cannulas.
Figure 7B:
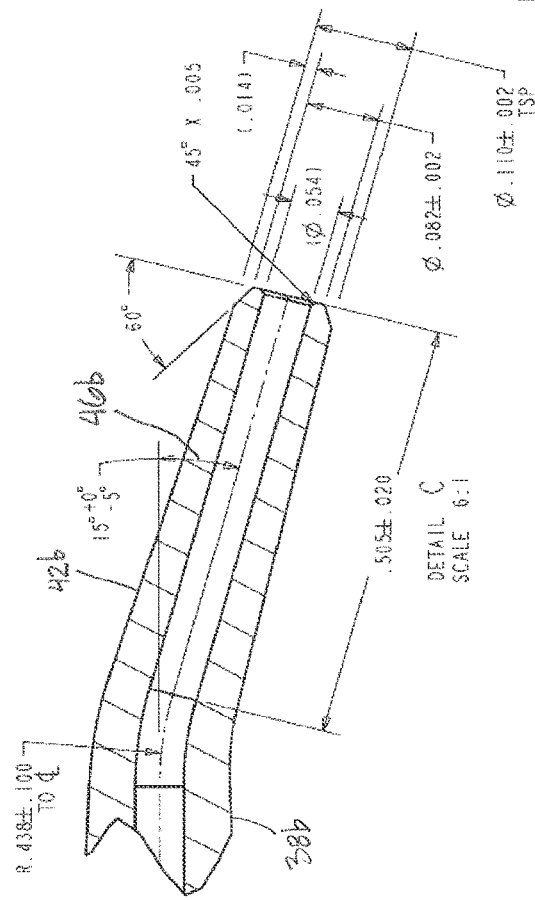
FIG. 7B depicts an enlarged cross-sectional view of a distal portion of the cannula of FIG. 7A.

Referring now to FIGS. 7A and 7B, side cross-sectional views are shown of a third embodiment 18b of the present cannulas. Cannula 18b is substantially similar to cannula 18, with the exception that angle 46b is substantially equal to 15 degrees. In some embodiments, angle 46b can be between 5 degrees and 20 degrees (e.g., substantially equal to either of, or between, 10 degrees and 15 degrees). In other embodiments, angle 46b can be greater than 60 degrees (e.g., equal to, or between any two of: 60, 70, 80, 90, and/or more degrees). As a further example, distal portion 42b can include a curved or hooked shape such that angle 46b is effectively larger than 90 degrees (e.g., equal to, or between any two of: 90, 120, 150, 180, and/or 180 degrees).

FIGS. 7A and 7B also include dimensions (in inches) for at least one exemplary embodiment of the present cannulas. Further, the difference between cannula 18a of FIG. 6 and cannula 18b of FIGS. 7A and 7B illustrate an embodiment of the present methods. In particular, some embodiments of the present methods (e.g., of making the present cannulas) comprise forming cannula 18b by bending (e.g., with a jig or the like) cannula 18a to angle 46.

Figure 8A:
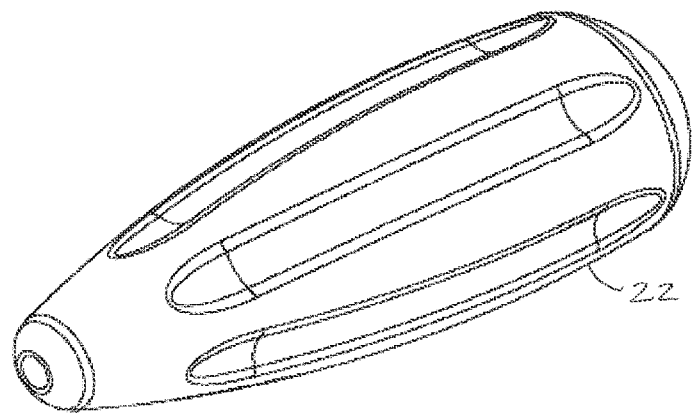
FIGS. 8A-8C depict various views of handle for use with the present cannulas.
Figure 8B:
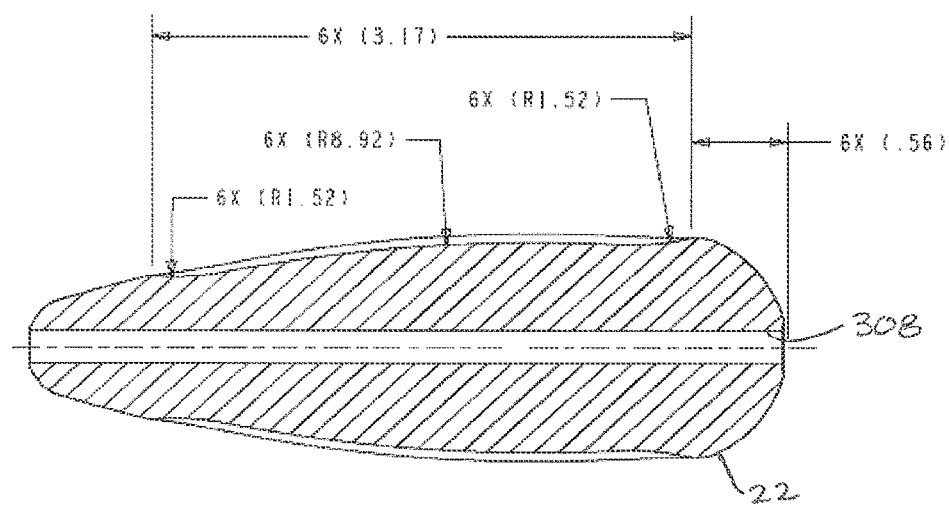
Figure 8C:
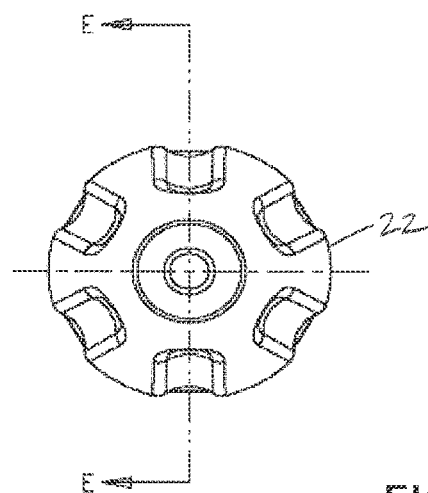

FIGS. 8A-8C depict various views of handle 22. FIG. 8B includes dimensions (in inches) for at least one exemplary embodiment of the present handles. As shown, handle 22 comprises a central longitudinal passage 312 configured to receive part of a primary portion (e.g., 38, 38a) of a cannula (e.g., 18, 18a, 18b), such as, for example, via a press fit or the like.

FIG. 9 depicts an exploded perspective view of a kit 400 comprising an embodiment 10 of the present apparatuses and a package 404 for the apparatus. In the embodiment shown, package 404 comprises a lower panel 408, a foam or other (e.g., molded plastic) receptacle 412 configured to receive apparatus 10 (including penetrator 14 and cannula 18), and an upper panel 416. In the embodiment shown, kit 400 also includes instructions 420 and a box 424. As indicated by the arrangement of panels 408 and 416, receptacle 412, and instructions 420, these components fit into box 424. In some embodiments, such as the one shown, cannula 18 (including handle 22) and/or penetrator 14 are sterile and/or sealed in plastic independently of receptacle 412.

Figure 10A:
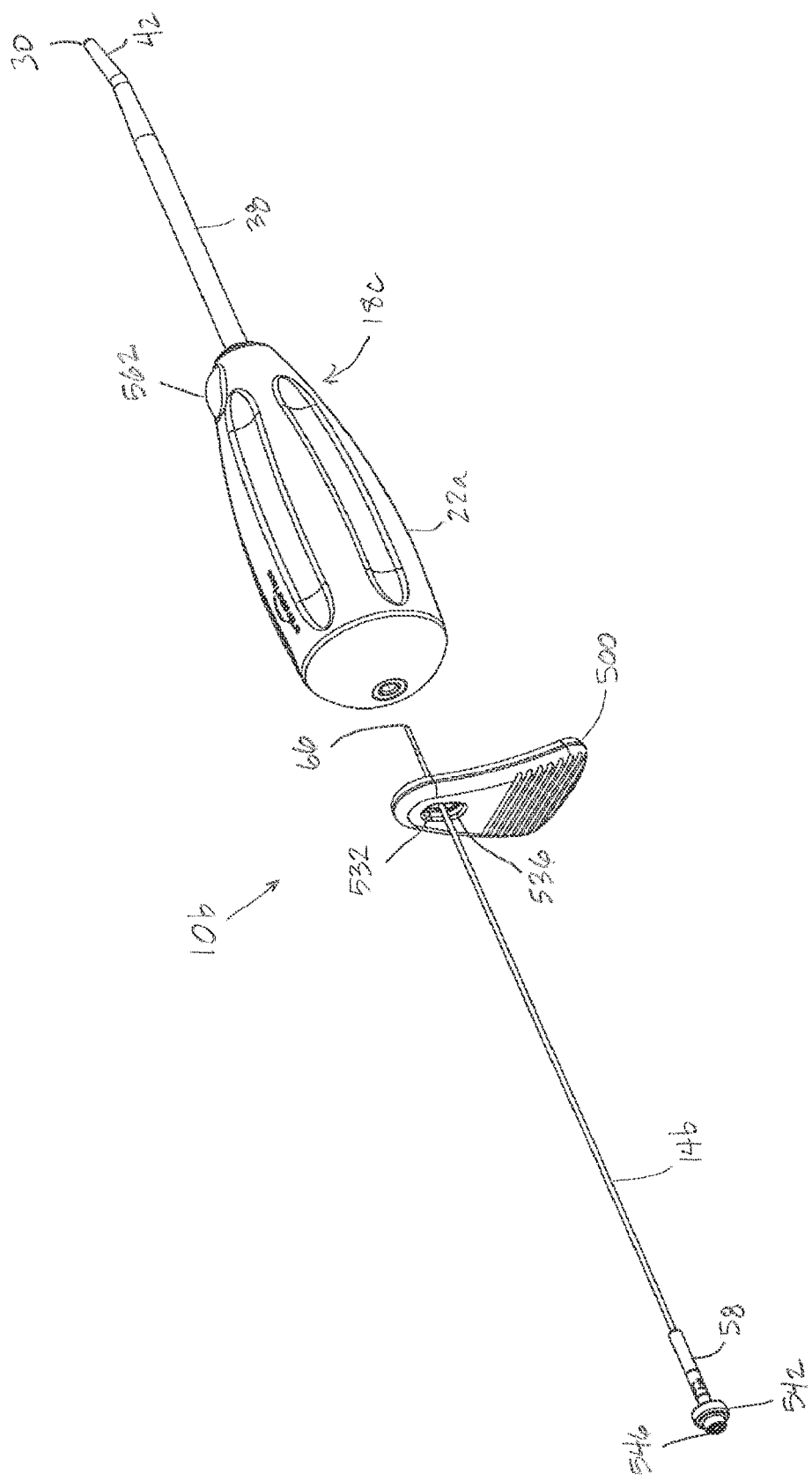
FIGS. 10A-10D depict various views of another embodiment of the present apparatuses that includes a penetrator removal tab in combination with the penetrator of FIG. 5A and a fourth embodiment of the present cannulas.
Figure 10B:
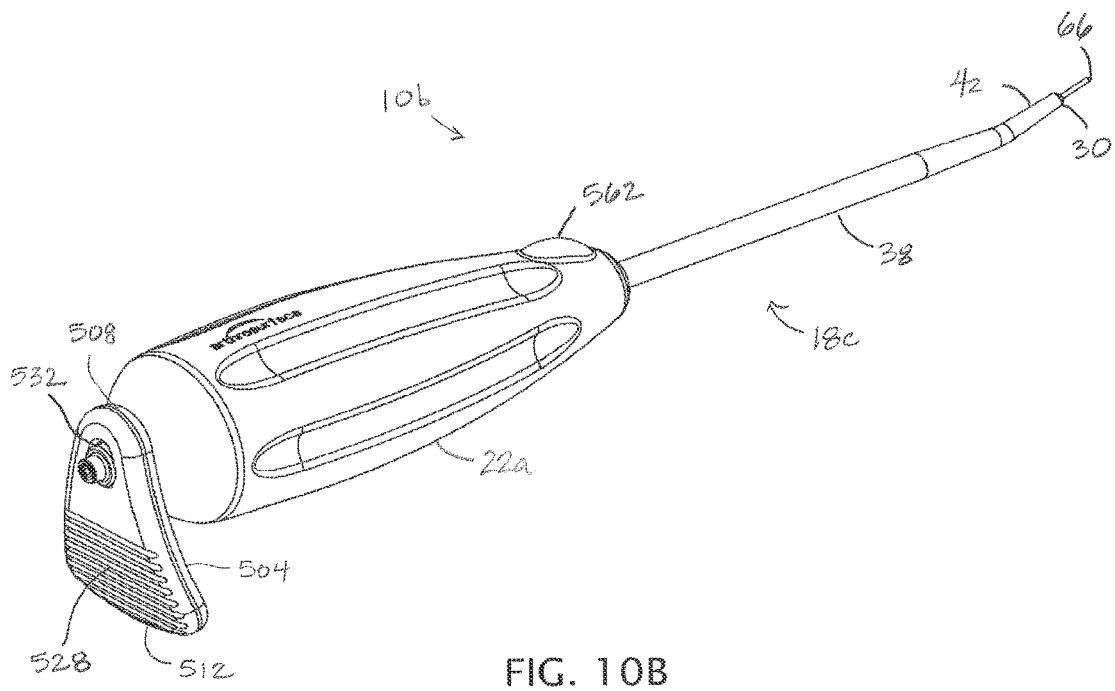
Figure 10C:
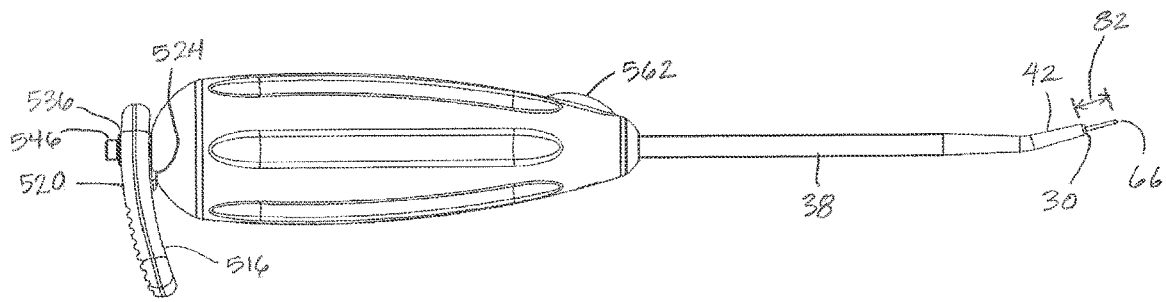
Figure 10D:
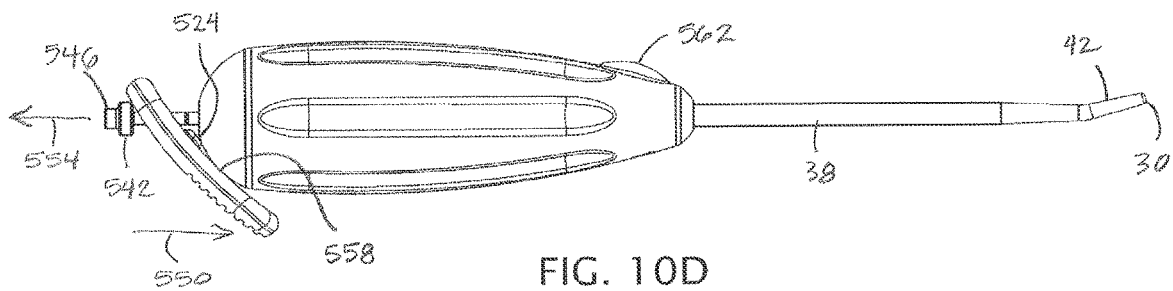

FIGS. 10A-10D depict various views of another embodiment 10b of the present apparatuses that includes a penetrator removal tab 500 in combination with a penetrator 14b and a fourth embodiment 18c of the present cannulas. In the embodiment shown, tab 500 comprises a body 504 with a first end 508, a second end 512, a distal side 516, and a proximal side 520. In the embodiment shown, distal side 516 is configured to face toward second end 30 of cannula 18c, and comprises a protrusion 524 configured to contact handle 22 to act as a fulcrum during use, as described in more detail below. In the embodiment shown, distal side 520 includes a plurality of grooves 528 to contact and resist slippage of a user's thumb during use. In other embodiments, grooves 528 may be omitted and/or substituted with a different type of texture. As shown in FIGS. 10C and 10D, body 504 has a curved or arcuate shape such that distal side 516 is concave and proximal side 520 is convex.

In the embodiment shown, body 504 includes an elongated opening 532 that is closer to first end 508 than to second end 512, and that is configured to receive enlarged head 58 of penetrator 14a as shown in FIGS. 10B and 10C. For example, in some embodiments, opening 516 can have a width (smaller transverse dimension) that is between 100% and 150% (e.g., between any two of: 100%, 110%, 120%, 130%, 140%, and 150%) of a corresponding transverse dimension (e.g., diameter 106) of enlarged head 58, and/or can have a height (larger transverse dimension) that is between 150% and 250% (e.g., between any two of: 150%, 175%, 200%, 225%, and 250%) of a corresponding transverse dimension (e.g., diameter 106) of enlarged head 58. The elongated shape of opening 532 permits tab 500 to pivot relative to enlarged head 58 (and overall penetrator 14b) to apply an axial removal force to penetrator 14b while minimizing any lateral force that might otherwise deflect and/or impede movement of the penetrator.

As shown, proximal side 520 of body 504 also includes a recess 536 configured to at least partially receive FIG. 10C) a corresponding flange 542 that is coupled to (e.g., unitary with) enlarged head 58. For example, in the embodiment shown, flange 542 is configured to be disposed over and coupled in fixed relation to proximal end 54 and enlarged head 58 of penetrator 14b. In his embodiment, flange 542 includes a neck 546 configured to be crimped and/or adhered via adhesive to enlarged head 58. In other embodiments, flange 542 may be unitary with enlarged head. As shown, flange 542 has a transverse dimension (e.g., diameter) that is larger than a corresponding transverse dimension (e.g., diameter) of opening 504 but smaller than a corresponding transverse dimension of recess 536. In some embodiments, enlarged head 58 is omitted and flange 542 and opening 528 (e.g., and recess 532) also limits the maximum penetration distance 82.

In use, a penetrator 14b (e.g., having flange 542 coupled to enlarged head 58) can be inserted through opening 528 and into cannula 18c such that tab 500 is disposed between flange 542 and handle 22a of cannula 18c. Second end 30 of cannula 18c can then be disposed in a desired location relative to a bone, and penetrator 14b can be impacted to drive distal end 66 of the penetrator into the bone. With distal end 66 disposed in the bone, a user can apply a force to proximal side 520 of tab 500 in direction 550 (toward second end 30 of cannula 18c) to cause tab 500 to pivot around protrusion 524 and apply a force to flange 542 to retract the penetrator in direction 524. In the embodiment shown, protrusion 524 is sized such that a second part of tab 500 (504) will also contact handle 22a at point 558 (such that protrusion once the penetrator is retracted by a distance about equal to or just larger than the maximum penetration distance (e.g., 82 of FIG. 2C) of the penetrator/cannula combination to prevent protrusion 524 from further acting as a fulcrum for tab 500. For example, limiting the retraction distance (e.g., to between 100% and 120% of maximum penetration distance 82) in this way can minimize the lateral force applied to enlarged head 58 during retraction of the penetrator and can facilitate reinsertion of the penetrator in a new location by minimizing the distance the penetrator must be advanced to bring its distal end (66) into initial contact with the bone at the new location.

In the embodiment shown, handle 22a is substantially similar to handle 22 with the exception that handle 22a includes a protrusion 562 that is aligned with distal portion 42 of cannula 18c. For example, in this embodiment, primary portion 38 of cannula 18c, distal portion 42 of cannula 18c, and protrusion 562 of handle 22d are each bisected by a single common plane. Protrusion 562 thus provides an indicator for a user of the orientation of distal portion 42 (e.g., even when distal portion 42 is disposed within a patient and out of the user's sight). In other embodiments, any suitable indicator may be used (e.g., a depression instead of a protrusion, an arrow printed or painted on handle 22, and/or the like).

Figure 11A:
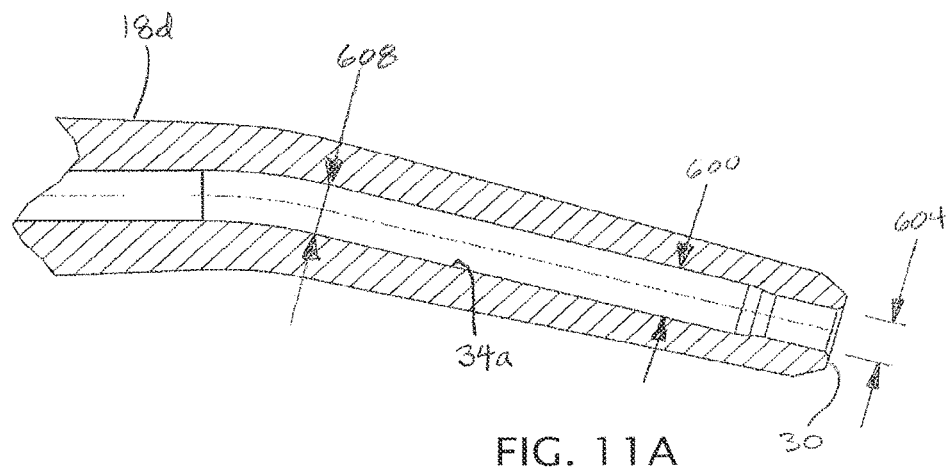
FIG. 11A depicts a cross-sectional view of a portion of a fourth embodiment of the present cannulas.
Figure 11B:
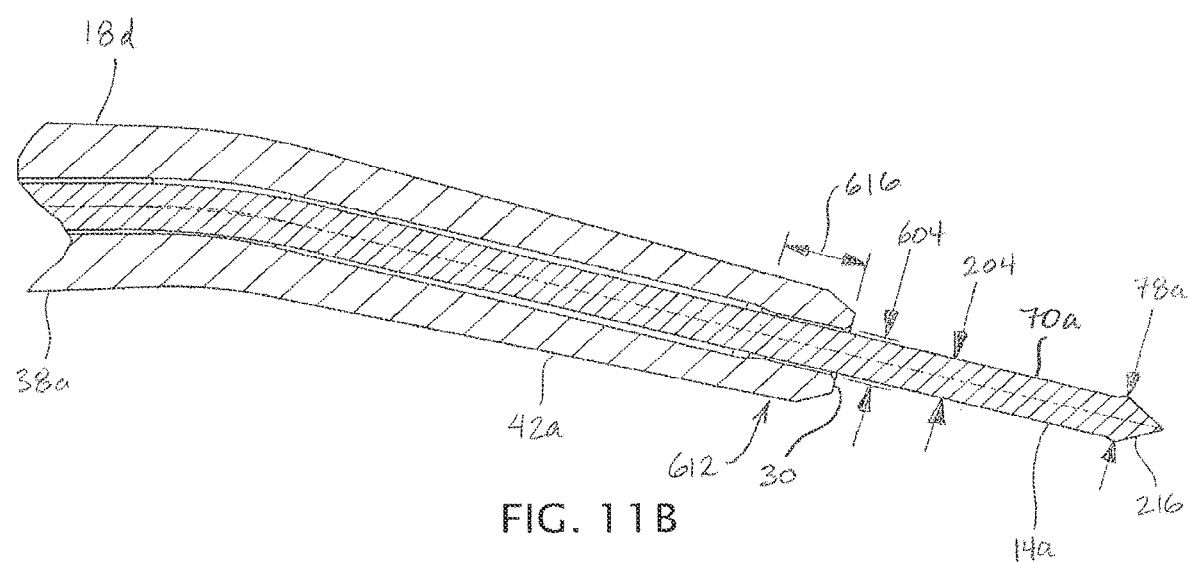
FIG. 11B depicts a cross-sectional view of a portion of the cannula of FIG. 11A with a penetrator of FIGS. 5A-5C disposed in the channel of the cannula.

FIG. 11A depicts a cross-sectional view of a portion of a fourth embodiment 18d of the present cannulas, and FIG. 11B depicts a cross-sectional view of the same portion of cannula 18d with a penetrator 14a disposed in channel 34a of the cannula. Cannula 18d is substantially similar to cannula 18b, with the exception that channel 34a cannula 18d includes a first transverse dimension 600 between first end (i.e., 26) and second end 30, and a second transverse dimension 604 at second end 30 that is smaller than first transverse dimension 600. In the embodiment shown, channel 34a also has a third transverse dimension 608 at a proximal end of distal portion 42a that is larger than second transverse dimension 604. Third transverse dimension 608 may, for example, be substantially equal to first transverse dimension 600. For example, in the embodiment shown, channel 34a has a circular cross-section with a diameter 600 that is substantially constant along a majority of the length of channel 34a.

In the embodiment shown, second transverse dimension 604 is substantially constant along a portion 612 having a length 616. In some embodiments, such as the one shown, length 616 is greater than second transverse dimension 604 and is also greater than first transverse dimension 600. In this embodiment, second transverse dimension 604 is larger than transverse dimension 78a of penetrator 14a, but second transverse dimension 604 is closer in size to transverse dimension 78a than to first transverse dimension 600. As with cannula 18b, transverse dimension 604 is large enough to permit penetration portion 70a of penetrator 14a to laterally flex (e.g., away from the center of the channel and toward to the center of curvature) around the bend or angle between primary portion 38a and distal portion 42a of cannula 18d. In this embodiment, however, the smaller second transverse dimension 604 (smaller relative to first transverse dimension 600) is configured to minimize lateral flexure of penetration portion 70a of penetrator 14a during insertion into and removal from bone (e.g., to ensure that microfractures are substantially circular rather than oval).

Figure 12:
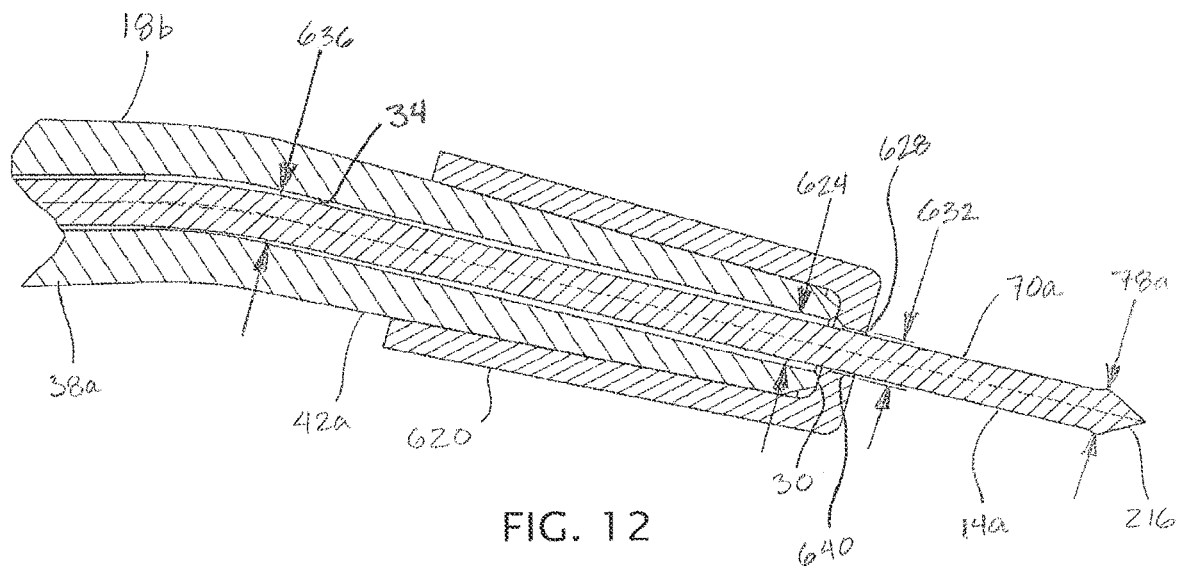
FIG. 12 depicts a cross-sectional view of a portion of the cannula of FIG. 7A with a guide member coupled to a distal end of the cannula.

FIG. 12 depicts a cross-sectional view of a portion of cannula 18b (FIGS. 7A-7B) with a guide member 620 coupled to distal or second end 30 of the cannula. In this embodiment, channel 34 of cannula 18b has a first transverse dimension 624 at second end 30 of the cannula. In this embodiment, guide member 620 has an opening 628 and is configured to be coupled to second end 30 of the cannula such that at least a portion of opening 628 is aligned with channel 34. In this embodiment, opening 628 has a transverse dimension 632 that is smaller than transverse dimension 624 of channel 34 at second end 30 of the cannula. In the embodiment shown, channel 34 also has a second transverse dimension 636 at a proximal end of distal portion 42a that is larger than transverse dimension 632 of opening 628. Second transverse dimension 636 may, for example, be substantially equal to first transverse dimension 624. For example, in the embodiment shown, channel 34 has a circular cross-section with a diameter 624 that is substantially constant along a majority of the length of channel 34.

In the embodiment shown, second transverse dimension 628 is substantially constant along a portion 640 having a length that is less than (e.g., equal to or greater than 40%, 50%, or a greater percentage of) transverse dimension 632. In this embodiment, transverse dimension 632 is larger than transverse dimension 78a of penetrator 14a, but transverse dimension 632 is closer in size to transverse dimension 78a than to first transverse dimensions 624. Transverse dimension 624 and 632 are large enough to permit penetration portion 70a of penetrator 14a to laterally flex (e.g., away from the center of the channel and toward to the center of curvature) around the bend or angle between primary portion 38a and distal portion 42a of cannula 18b. In this embodiment, however, the smaller transverse dimension 632 (smaller relative to first transverse dimension 624) is configured to minimize lateral flexure of penetration portion 70a of penetrator 14a during insertion into and removal from bone (e.g., to ensure that microfractures are substantially circular rather than oval).

Figure 13:
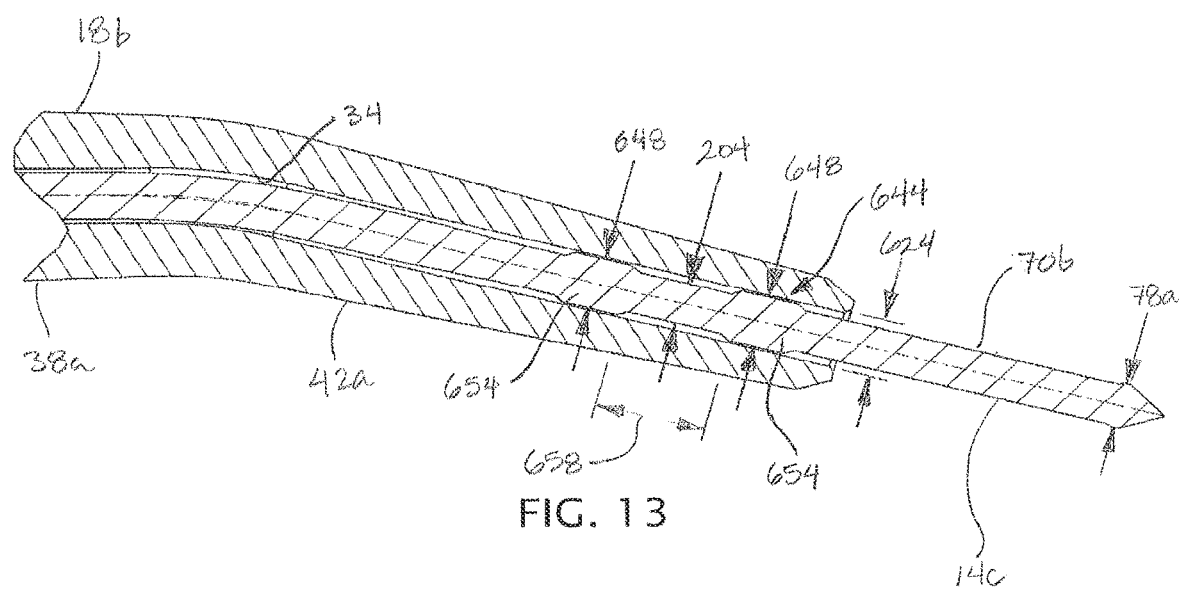
FIG. 13 depicts a cross-sectional view of a portion of the cannula of FIG. 7A with another embodiment of the present penetrators disposed in the channel of the cannula.

FIG. 13 depicts a cross-sectional view of a portion of cannula 18b with another embodiment 14c of the present penetrators disposed in channel 34 of the cannula. Penetrator 14c is substantially similar to penetrator 14a with the exception that penetration portion 70b of penetrator 14c includes a guide portion 644 spaced from distal end 66 (by a distance at least as large as the desired penetration distance) and having a transverse dimension 648 that is larger than transverse dimension 204 of penetration portion 70b. In the embodiment shown, guide portion 644 includes two segments 654 spaced apart from each other and each having a transverse dimension 648 that is larger than the smallest transverse dimension 204 of penetrator 14c. In this embodiment, segments 654 are spaced apart from each other by a distance 658 that is configured to permit segments 654 to pass through the curve in channel 34 between proximal portion 38a and distal portion 42a of cannula 18b. For example, in the embodiment shown, distance 658 is greater than transverse dimension 624 of channel 34, and is greater the length of each segment 654.

In the embodiment shown, each segment 654 also has a length that is equal to or greater than their transverse dimension 648. The elongated outer profile of segments 654 resists longitudinal rotation of each individual segment and thereby resist lateral flexure and misalignment of penetration portion 70b. In other embodiments, each segment 654 can have a length that is equal to or greater than 40%, 50%, or a greater percentage of transverse dimension 648. In the embodiment shown, each segment 654 has a circular cross-sectional shape, but in other embodiments may have any suitable cross-sectional shape (e.g., triangular, square, star-shaped with three, four, five, or more points, and/or any other shape that permits the apparatus to function as described). In this embodiment, transverse dimension 648 can be equal to or larger than transverse dimension 78a of penetrator 14c, but transverse dimension 648 is closer in size to transverse dimension 624 than to transverse dimension 204. The configuration (including distance from distal end 66, shape, and transverse dimension 648) of guide portion 640 is such that guide portion 640 will slide through channel 34 past the bend between proximal portion 38a and distal portion 42a, but will also maintain axial alignment of the part of penetration portion 70b between guide portion 640 and distal end 66 when guide portion 640 is located entirely in distal portion 42a. In this embodiment, the larger transverse dimension 648 (larger relative to transverse dimension 204) is configured to minimize lateral flexure of penetration portion 70b of penetrator 14c during insertion into and removal from bone (e.g., to ensure that microfractures are substantially circular rather than oval).

Figure 14A:
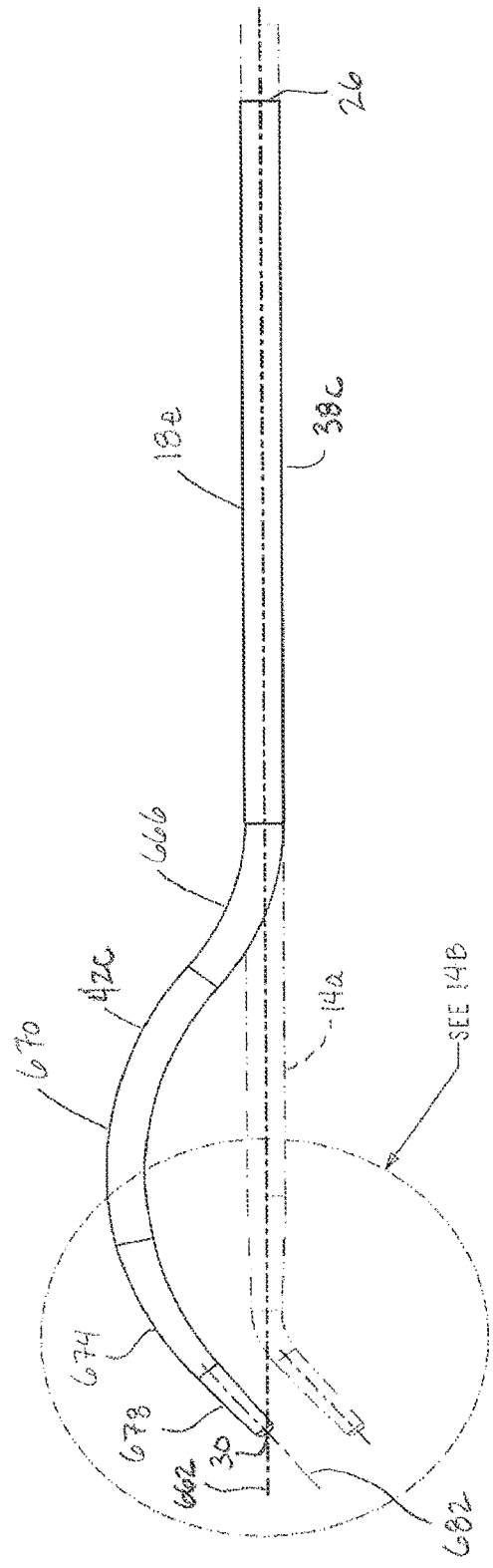
FIG. 14A depicts a side view of a fifth embodiment of the present cannulas.
Figure 14B:
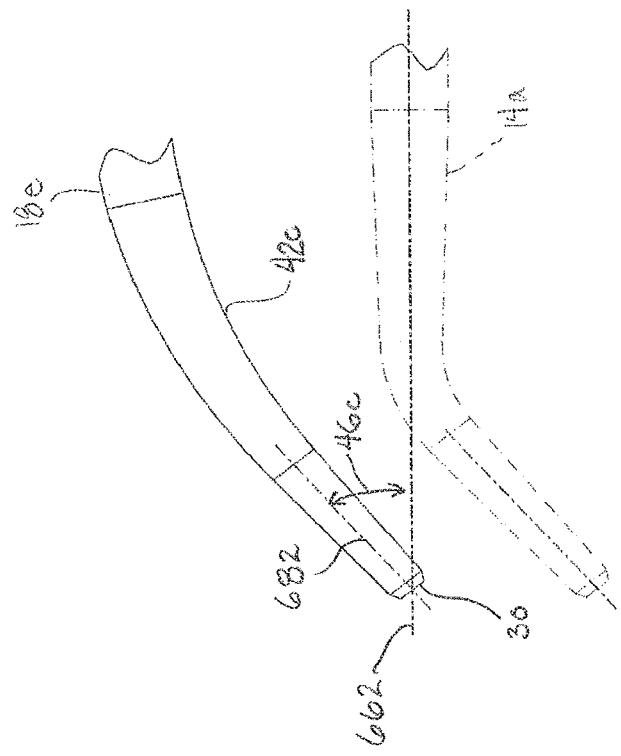
FIG. 14B depicts an enlarged side view of the cannula of FIG. 14A.

FIG. 14A depicts a side view of a fifth embodiment 18e of the present cannulas, and FIG. 14B depicts an enlarged side view of cannula 18e. Cannula 18e is similar in several respects to cannula 18b with the primary exception that second end 30 (and the corresponding second end of channel 34) is aligned with first end 26 (and the corresponding first end of the channel) and/or with longitudinal axis 662 of primary portion 38c. In the embodiment shown, distal portion 42c is longer than distal portion 42a of cannula 18a to accommodate a relatively large curved portion that curves in a first direction away from axis 662 and then curves back toward axis 662 to a linear portion that terminates at second end 30. In this embodiment, distal portion 42c includes a plurality of curved segments and, more particularly, includes an arcuate first segment 666 extending from a distal end of primary portion 38c, an arcuate second segment 670 extending from and curving in a direction opposite to the curvature of arcuate first segment 666, an arcuate third segment 674 extending from and curving in the same direction as the curvature of arcuate second segment 670, and a linear fourth segment 678 extending from arcuate third segment 674, as shown. In this embodiment, a longitudinal axis 682 of linear fourth segment 678 intersects axis 662 of primary portion 38c at second end 30 of the cannula. In the embodiment shown, arcuate second segment 670 and third arcuate segment 674 each has a radius of curvature that is larger than that of first arcuate segment 666.

In the embodiment shown, angle 46c between second end 30 (axis 682) and first end 26 (axis 662) is greater than angle 46b (FIG. 7B). The depicted configuration in which distal portion 42c curves away from and then back toward the longitudinal axis (662) of primary portion 38c permits larger values of angle 46c while still permitting a penetrator to advance and retract within in the cannula. Angle 46c can, for example, be equal to or greater than any one of, and/or between any two of: 15, 20, 25, 30, 35, 40, 45, 50, 55, 60, or more degrees). In addition to permitting greater tip angles, the alignment of second end 30 with first end 26 (and/or with longitudinal axis 662) has shown through experimentation to make the apparatus (especially with greater tip angles) easier to use. For example, because second end 30 is aligned with first end 26, an impact force or impulse applied to a proximal end or head of a penetrator within cannula 18e is directed in a straight line (axis 662) on which second end 30 lies. The effect is to make the apparatus easier to control during use, resulting in more consistent, round microfractures (as opposed to oval microfractures or microfractures that are misplaced due to sliding of the cannula.

Figure 15A:
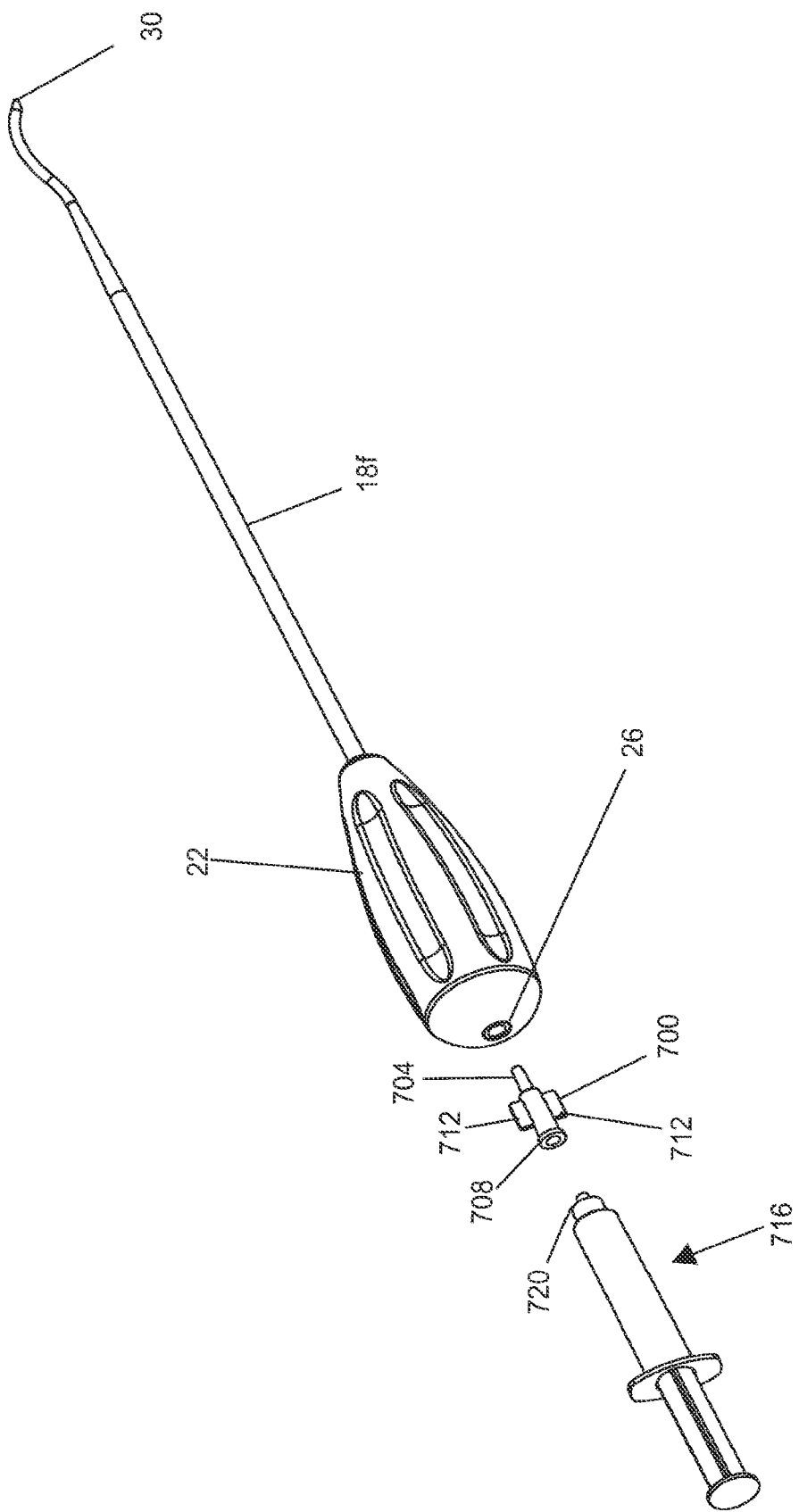
FIG. 15A-15B depict perspective views of a sixth embodiment of the present apparatuses shown with an adapter for coupling a syringe to the cannula of the apparatus.
Figure 15B:
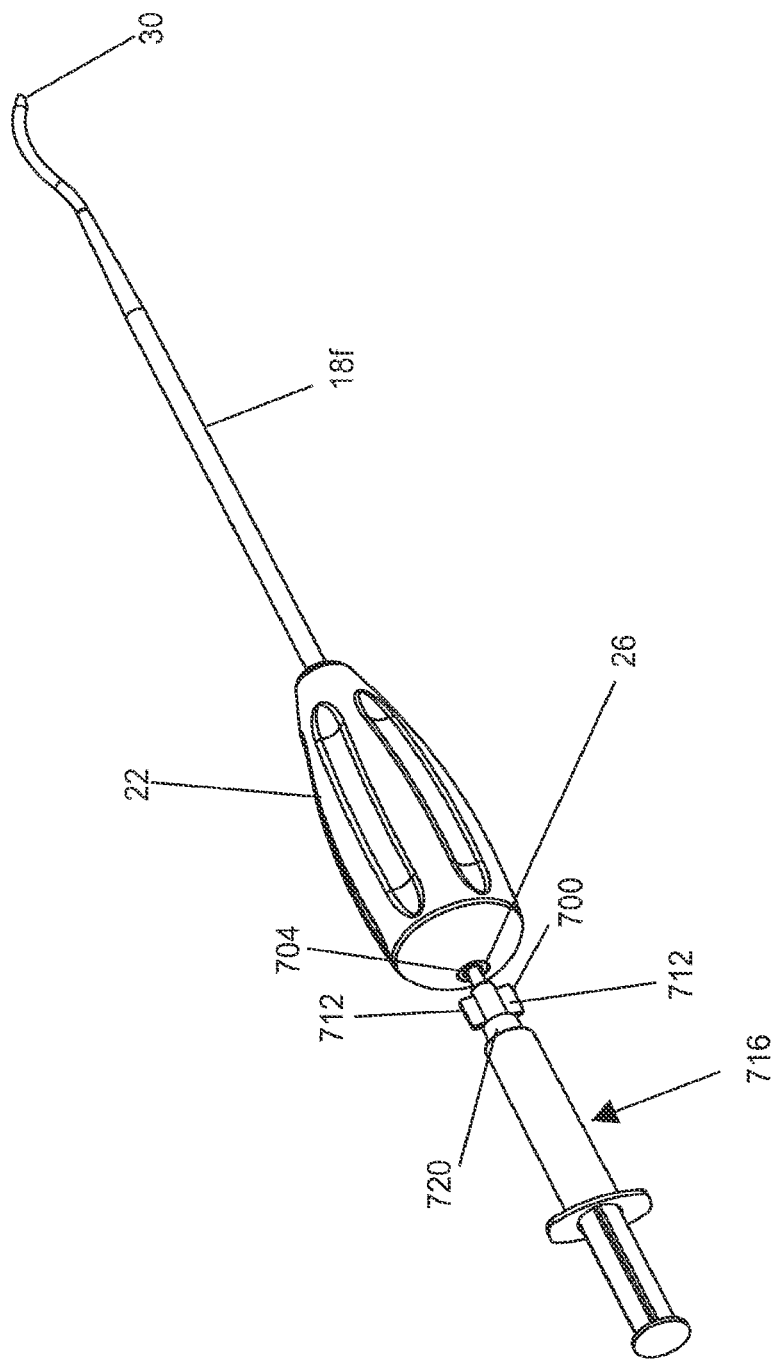

FIG. 15A and FIG. 15B depict perspective views of a sixth embodiment of the present apparatuses having a cannula 18f, and shown with an adapter 700 configured to couple cannula 18f to a fluid source (e.g., a syringe). The sixth embodiments is substantially similar to the fifth embodiment with the primary exception that distal end 30 of cannula 18f is disposed at a smaller angle relative to first end 26 than corresponding angle 46c of cannula 18e of FIGS. 14A and 14B.

In the embodiment shown, adapter 700 is includes a first end 704 configured to be coupled to (e.g., inserted into) first end 26 of cannula 18f and a second end 708 configured to be coupled to a fluid source, and a channel extending between first end 704 and second end 708 to facilitate delivery of a fluid via distal end 30 of the cannula (e.g., to a microfracture in an articular surface of a patient). In this embodiment, first end 704 includes a tapered, frusto-conical outer surface sized to fit into the channel at first end 26 of cannula 18f. In some embodiments, the channel of adapter 700 has an inner diameter of 5 mm or smaller (e.g., less than 4 mm, 3 mm, 2 mm, or smaller) and/or adapter 700 has at least one outer diameter (e.g., the smallest outer diameter of tapered first end 704) of less than 6 mm to facilitate insertion of first end 704 into the channel of cannula 18f at first end 26.

In the embodiment shown, adapter 700 includes protrusions 712 to facilitate manipulation of the adapter by a user (e.g., to connect the adapter to the cannula or to the fluid source). In the embodiment shown, protrusions 712 extend outwardly at least 3 mm from an adjacent exterior surface of adapter 700. Protrusions 712 can also be configured facilitate mechanized manipulation of adapter 700. For example, a surgical robot may engage the protrusions to couple adapter 700 to a fluid source and/or the cannula.

As shown, adapter 700 can be configured to be coupled to a syringe 716. Other fluid sources may also or alternatively be used (e.g., drip bags or tubing). In the embodiment shown, second end 708 of adapter 700 includes a threads (e.g., a luer lock or luer fitting) configured to be coupled to corresponding threads (e.g., luer lock or luer fitting) 720 of the syringe.

Adapter 700 is especially suited to enable delivery (e.g., in some of the present methods) of fluids to an articular surface of a patient (e.g., via one of the present cannulas), such as, for example, to a microfracture in an articular surface of a patient. Examples of fluids that may be delivered include saline, hyaluronic acid, platelet-rich-plasma, human tissue allografts such as those derived from amniotic fluid and/or membranes, growth factors, proteins, and/or cellular-based therapies.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, penetrator 18 and/or channel 34 can have any suitable cross-sectional shape (e.g., triangular, square, rectangular, and/or the like) that permits the present apparatuses and methods to function as described in this disclosure. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus comprising:
a cannula having a first end, a second end, and a channel extending between the first end and the second end, the channel having a first transverse dimension between the first end and the second end and having a second transverse dimension at the second end that is smaller than the first transverse dimension, the channel tapering from the second transverse dimension to the first transverse dimension at a point closer to the second end than to the first end, the channel having a second end that is disposed at an angle relative to a first end of the channel; and
a penetrator having a distal end and a first transverse dimension, the penetrator configured to be disposed in the channel of the cannula such that the penetrator is movable between a retracted position and an extended position in which the distal end extends beyond the second end of the cannula by a penetration distance;
where the penetrator is configured to be moved from the retracted position to the extended position substantially without rotation of the penetrator to form in subchondral bone a microfracture.

2. The apparatus of claim 1, where the first transverse dimension is substantially constant along a majority of the length of the channel.

3. The apparatus of claim 1, where the cannula has a primary portion and a distal portion between the primary portion and the second end, the distal portion configured such that:
the channel has a third transverse dimension at a proximal end of the distal portion that is larger than the second transverse dimension.

4. The apparatus of claim 3, where the third transverse dimension is substantially equal to the first transverse dimension.

5. The apparatus of claim 1, where the distal portion of the cannula includes a plurality of curved segments.

6. The apparatus of claim 1, where the penetration distance is at least 5 times greater than the first transverse dimension of the channel.

7. The apparatus of claim 6, where the first transverse dimension is less than 1.2 millimeters (mm).

8. The apparatus of claim 7, where the penetration distance is at least 5 millimeters (mm).

9. The apparatus of claim 1, where the first transverse dimension is less than 1.2 millimeters (mm).

10. The apparatus of claim 9, where the penetration distance is at least 5 millimeters (mm).

11. The apparatus of claim 9, where the penetrator is configured to be moved from the retracted position to the extended position substantially without rotation of the penetrator to form in subchondral bone a microfracture having a depth of at least 5 mm.

12. The apparatus of claim 1, where the penetrator is configured to be manually moved from the retracted position to the extended position.

13. The apparatus of claim 1, where the penetrator has an enlarged head, and the penetration distance is limited by the enlarged head contacting the cannula.

14. The apparatus of claim 1, where a coating is disposed on at least the penetration portion of the penetrator.

15. The apparatus of claim 1, where the penetrator includes a primary portion and a penetration portion, the primary portion having a circular cross-section, the penetration portion disposed between the primary portion and the distal end, the penetration portion having a circular cross-section that is smaller than the circular cross-section of the primary portion.

16. The apparatus of claim 15, where the distal end includes a pointed tip with a cross-sectional shape defined by a tip angle of 60 degrees or greater.

17. The apparatus of claim 16, where the tip angle is bisected by a central longitudinal axis of the penetration portion, and the tip angle is greater than 90 degrees.

18. The apparatus of claim 1, further comprising:
a penetrator removal tab coupled to the penetrator and configured to retract the penetrator relative to the cannula.

19. The apparatus of claim 18, where:
the cannula includes a handle,
the penetrator includes a flange,
the penetrator removal tab includes an opening that is has at least one transverse dimension that is smaller than a transverse dimension of the flange; and
the penetrator removal tab is configured to be disposed between the handle and the flange with the penetrator extending through the opening.

20. The apparatus of claim 19, where the penetrator removal tab includes a protrusion configured to extend toward the second end of the cannula and contact the handle to act as a fulcrum for pivoting the penetrator removal tab.

* * * * *